United States Patent
Mokelke et al.

(10) Patent No.: US 9,763,586 B2
(45) Date of Patent: Sep. 19, 2017

(54) SYSTEM AND METHOD FOR LOCATING NEURAL TISSUE

(71) Applicant: Cardiac Pacemakers, Inc., St. Paul, MN (US)

(72) Inventors: Eric A. Mokelke, White Bear Lake, MN (US); David J. Ternes, Roseville, MN (US); Allan Charles Shuros, St. Paul, MN (US); Hong Cao, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 194 days.

(21) Appl. No.: 14/570,347

(22) Filed: Dec. 15, 2014

(65) Prior Publication Data
US 2015/0173636 A1 Jun. 25, 2015

Related U.S. Application Data

(60) Provisional application No. 61/918,269, filed on Dec. 19, 2013.

(51) Int. Cl.
*A61B 5/00* (2006.01)
*A61B 5/04* (2006.01)
(Continued)

(52) U.S. Cl.
CPC ........ *A61B 5/04001* (2013.01); *A61B 5/0538* (2013.01); *A61B 5/4893* (2013.01);
(Continued)

(58) Field of Classification Search
CPC ..... A61B 5/04; A61B 5/04001; A61B 5/0488; A61B 5/053; A61B 5/0531; A61B 5/0538;
(Continued)

(56) References Cited

U.S. PATENT DOCUMENTS

| 5,243,980 A | 9/1993 | Mehra |
| 5,341,807 A | 8/1994 | Nardella |

(Continued)

FOREIGN PATENT DOCUMENTS

| CN | 101868280 A | 10/2010 |
| CN | 105828870 A | 8/2016 |

(Continued)

OTHER PUBLICATIONS

Cao, Hong, et al., "Using Electrical Impedance to Predict Catheter-Endocardial Contact During RF Cardiac Ablation", IEEE Transactions on Biomedical Engineering, 49(3), (Mar. 2002), 247-253.

(Continued)

*Primary Examiner* — Max Hindenburg
(74) *Attorney, Agent, or Firm* — Schwegman Lundberg & Woessner, P.A.

(57) ABSTRACT

An example of a system comprises a patch of electrodes for placement on tissue containing neural tissue, and a tissue tester configured to measure an electrical characteristic of tissue. The tissue tester may include a test controller and switches. The test controller and the switches may be configured to connect different combinations of the electrodes to create subsets of two or more electrodes to measure the electrical characteristic of tissue using the subsets. The test controller may be configured to measure an electrical characteristic of tissue using the subsets within the set of electrodes placed on the tissue, and compare measurements of the electrical characteristic and identify a neural target for a therapy based on the comparison of the measurements of the electrical characteristic for tissue at the neural target relative to adjacent non-neural tissue.

12 Claims, 16 Drawing Sheets

(51) Int. Cl.
*A61B 18/12* (2006.01)
*A61N 1/36* (2006.01)
*A61B 5/053* (2006.01)
*A61B 18/14* (2006.01)
*A61N 1/05* (2006.01)
*A61B 18/00* (2006.01)

(52) U.S. Cl.
CPC ...... *A61B 18/1206* (2013.01); *A61B 18/1492* (2013.01); *A61N 1/0551* (2013.01); *A61N 1/36128* (2013.01); *A61N 1/36139* (2013.01); *A61N 1/36185* (2013.01); *A61B 5/6848* (2013.01); *A61B 2018/00404* (2013.01); *A61B 2018/00434* (2013.01); *A61B 2018/00511* (2013.01); *A61B 2018/00577* (2013.01); *A61B 2018/124* (2013.01); *A61B 2562/046* (2013.01)

(58) Field of Classification Search
CPC . A61B 5/4893; A61B 5/6848; A61B 18/1206; A61B 18/1492; A61B 2018/00434; A61B 2018/00577; A61B 2018/124; A61B 2018/00404; A61B 2018/00511; A61N 1/18; A61N 1/36139; A61N 1/36185; A61N 1/36128
See application file for complete search history.

(56) References Cited

U.S. PATENT DOCUMENTS

| | | |
|---|---|---|
| 5,411,531 A | 5/1995 | Hill et al. |
| 5,507,784 A | 4/1996 | Hill et al. |
| 6,514,248 B1 | 2/2003 | Eggers |
| 7,477,763 B2 | 1/2009 | Willis et al. |
| 7,610,078 B2 | 10/2009 | Willis |
| 7,633,502 B2 | 12/2009 | Willis et al. |
| 7,715,915 B1 | 5/2010 | Ryu et al. |
| 7,769,441 B2 | 8/2010 | Foreman et al. |
| 7,769,446 B2 | 8/2010 | Moffitt et al. |
| 7,826,899 B1 | 11/2010 | Ryu et al. |
| 7,860,563 B2 | 12/2010 | Foreman et al. |
| 7,983,748 B2 | 7/2011 | Ruse |
| 8,034,051 B2 | 10/2011 | Martin et al. |
| 8,106,905 B2 | 1/2012 | Markowitz et al. |
| 8,208,991 B2 | 6/2012 | Markowitz et al. |
| 8,214,018 B2 | 7/2012 | Markowitz et al. |
| 8,241,273 B2 | 8/2012 | Whayne et al. |
| 8,260,395 B2 | 9/2012 | Markowitz et al. |
| 8,315,696 B2 | 11/2012 | Schwartz |
| 8,340,751 B2 | 12/2012 | Markowitz et al. |
| 8,348,939 B2 | 1/2013 | Martin et al. |
| 8,352,033 B2 | 1/2013 | Kroll |
| 8,424,536 B2 | 4/2013 | Markowitz et al. |
| 8,449,472 B2 | 5/2013 | Ryu et al. |
| 8,465,479 B2 | 6/2013 | Whayne et al. |
| 8,467,863 B2 | 6/2013 | Kahlert et al. |
| 8,494,608 B2 | 7/2013 | Markowitz et al. |
| 8,504,132 B2 | 8/2013 | Friedman et al. |
| 8,620,422 B2 | 12/2013 | Kieval et al. |
| 9,205,263 B2 * | 12/2015 | King ................ A61N 1/36071 |
| 9,248,269 B2 * | 2/2016 | Kipke ................ A61B 5/04001 |
| 9,381,356 B2 * | 7/2016 | Parker ................ A61B 5/04001 |
| 9,386,934 B2 * | 7/2016 | Parker ................ A61N 1/36125 |
| 9,433,787 B2 * | 9/2016 | Elias ................ A61N 1/36103 |
| 9,510,762 B2 * | 12/2016 | Datovech ........... A61B 5/04085 |
| 2003/0100924 A1 | 5/2003 | Foreman et al. |
| 2006/0085049 A1 | 4/2006 | Cory et al. |
| 2006/0111745 A1 | 5/2006 | Foreman et al. |
| 2006/0111746 A1 | 5/2006 | Foreman et al. |
| 2007/0191895 A1 | 8/2007 | Foreman et al. |
| 2008/0009853 A1 | 1/2008 | Martin et al. |
| 2008/0091243 A1 | 4/2008 | Ternes |
| 2008/0275439 A1 | 11/2008 | Francischelli et al. |
| 2009/0216290 A1 | 8/2009 | Ruse et al. |
| 2009/0264727 A1 | 10/2009 | Markowitz et al. |
| 2009/0264740 A1 | 10/2009 | Markowitz et al. |
| 2009/0264744 A1 | 10/2009 | Markowitz et al. |
| 2009/0264745 A1 | 10/2009 | Markowitz et al. |
| 2009/0264750 A1 | 10/2009 | Markowitz et al. |
| 2009/0264771 A1 | 10/2009 | Houben et al. |
| 2009/0264778 A1 | 10/2009 | Markowitz et al. |
| 2010/0100160 A1 | 4/2010 | Edman et al. |
| 2010/0179524 A1 | 7/2010 | Whayne et al. |
| 2010/0217249 A1 | 8/2010 | Whayne et al. |
| 2011/0015690 A1 | 1/2011 | Ryu et al. |
| 2011/0046618 A1 | 2/2011 | Minar et al. |
| 2011/0066200 A1 | 3/2011 | Foreman et al. |
| 2011/0137362 A1 | 6/2011 | Foreman et al. |
| 2011/0144509 A1 | 6/2011 | Kahlert et al. |
| 2011/0152712 A1 | 6/2011 | Cao et al. |
| 2011/0313413 A1 | 12/2011 | Martin et al. |
| 2012/0059255 A1 | 3/2012 | Paul et al. |
| 2012/0130232 A1 | 5/2012 | Markowitz et al. |
| 2012/0150021 A1 | 6/2012 | Schwartz |
| 2012/0157804 A1 | 6/2012 | Rogers et al. |
| 2012/0190993 A1 | 7/2012 | Markowitz et al. |
| 2012/0226110 A1 | 9/2012 | Markowitz et al. |
| 2012/0265198 A1 | 10/2012 | Crow et al. |
| 2012/0271299 A1 | 10/2012 | Whayne et al. |
| 2013/0041235 A1 | 2/2013 | Rogers et al. |
| 2013/0123773 A1 | 5/2013 | Schwartz |
| 2013/0131746 A1 | 5/2013 | Simon et al. |
| 2013/0144365 A1 | 6/2013 | Kipke et al. |
| 2013/0158545 A1 | 6/2013 | Govari et al. |

FOREIGN PATENT DOCUMENTS

| | | |
|---|---|---|
| JP | 2011529732 A | 12/2011 |
| WO | WO-2009090682 A1 | 7/2009 |
| WO | WO-2010014686 A1 | 2/2010 |
| WO | WO-2012138782 A1 | 10/2012 |
| WO | WO-2015095024 A2 | 6/2015 |
| WO | WO-2015095024 A3 | 6/2015 |

OTHER PUBLICATIONS

Chen, Shao-Liang, et al., "Percutaneous pulmonary artery denervation completely abolishes experimental pulmonary arterial hypertension in vivo", EuroIntervention, 9, (Mar. 2013), 269-276.

Chen, Shao-Liang, et al., "Pulmonary artery denervation to treat pulmonary arterial hypertension: a single-center, prospective, first-in-man PADN-1 study", Journal of the American College of Cardiology (2013), doi: 10.1016/j.jacc.2013.05,075., Accepted Manuscript, (2013), 35 pgs.

Desimone, C. V, et al., "Percutaneous autonomic neural modulation: a novel technique to treat cardiac arrhythmia", Cardiovasc Revasc Med., 14(3), (May-Jun. 2013), 144-8.

Kapa, Suraj, et al., "The Autonomic Nervous System in Cardiac Electrophysiology: An Elegant Interaction and Emerging Concepts", Cardiology in Review, 18(6), (Nov.-Dec. 2010), 275-284.

Malcolme-Lawes, L. C, et al., "Characterization of the left atrial neural network and its impact on autonomic modification procedures.", Circ Arrhythm Electrophysiol., 6(3), (Jun. 2013) 632-40.

Prokhorov, E., et al,, "In vivo impedance measurements on nerves and surrounding skeletal muscles in rats and human body", Mad Biol Eng Comput., 40(3), (May 2002), 323-6.

Zhang, Yong, et al., "Ganglionated Plexi Ablation for Atrial Fibrillation", Ganglionated Plexi Ablation for Atrial Fibrillation, Atrial Fibrillation—Basic Research and Clinical Applications, Prof. Jong-Il Choi (Ed.), ISBN: 978-953-307-399-6, InTech, DOI: 10.5772/26461., Available from: http://www.intechopen.com/books/atrial-fibrillation-basic-research-and-clinical-applications/ganglionated-plexi-ablation-for-atrial-fibrillation, (2012), 17 pgs.

"European Application Serial No. , Response filed Feb. 3, 2017 to Communication Pursuant to Rules 161(1) and 162 EPC mailed Jul. 26, 2016", 8 pgs.

"International Application Serial No. PCT/US2014/070299, International Preliminary Report on Patenability mailed Jun. 30, 2016", 10 pgs.

(56) References Cited

OTHER PUBLICATIONS

"International Application Serial No. PCT/US2014/070299, International Search Report mailed Jun. 30, 2015", 7 pgs.
"International Application Serial No. PCT/US2014/070299, Invitation to Pay Additional Fees and Partial Search Report mailed Apr. 13, 2015", 6 pgs.
"International Application Serial No. PCT/US2014/070299, Written Opinion mailed Jun. 30, 2015", 8 pgs.
"Chinese Application Serial No. 201480069460.8, Office Action dated Jun. 28, 2017", w/ English translation, 18 pgs.
"Japanese Application Serial No. 2016-541086, Office Action dated May 16, 2017", With English Translation.

* cited by examiner

SYSTEM AND METHOD FOR LOCATING NEURAL TISSUE

CLAIM OF PRIORITY

This application claims the benefit of priority under 35 U.S.C. §119(e) of U.S. Provisional Patent Application Ser. No. 61/918,269, filed on Dec. 19, 2013, which is herein incorporated by reference in its entirety.

TECHNICAL FIELD

This document relates generally to medical devices, and more particularly, to systems, devices and methods for locating neural tissue.

BACKGROUND

Therapies applied to neural tissue may include, but are not limited to, electrical stimulation to enhance nerve activity, electrical stimulation to reduce or block nerve activity, and ablation of neural pathways. However, it can be difficult and time consuming to find the neural target for the therapy.

For example, it has been proposed to reduce blood pressure by electrically stimulating baroreceptor regions to induce a baroreflex response. Baroreceptors play an important role in regulating blood pressure, and are located throughout the body, but primarily in the arch of the aorta and the carotid sinuses of the left and right internal carotid arteries. Through a negative feedback baroreflex system, the central nervous system can regulate the blood pressure to maintain the blood pressure at a relatively stable level. For example, arterial pressure that causes stretch triggers the baroreflex to send nerve impulses to the brain which responds by controlling the pumping activity of the heart and blood vessel dilation to reduce the blood pressure.

The blood pressure response can fluctuate dramatically when different areas of the baroreceptor region are stimulated. For example, the blood pressure response at a first site within the baroreceptor region can be significantly different than the blood pressure response at a second site within the baroreceptor region. Animal experiments indicate responses can dramatically fluctuate spatially within 1 mm; and yet the carotid sinus area in humans is rather large (e.g. typically about 2 cm×1 cm). Thus, the implantation of a baromodulation device to stimulate a small baroreceptor region in the carotid sinus usually requires extensive mapping of the internal carotid arteries in order to find a desirable stimulation location along the carotid artery that provides an effective or that appears to provide one of the largest possible blood pressure responses if not the largest response. Currently, surgeons manually hold one or more electrode(s) at various locations near the carotid sinus to map the baroreceptor region during an implantation procedure. Mapping a tissue region to find candidate neural targets may take up to several hours. This procedure takes significant time and effort due to the difficulty of manually positioning the electrode and maintaining steady and consistent blood pressure. Longer procedure times also undesirably expose the patient to longer anesthesia times. Thus, the clinical procedure is often unable to access a full mapping area. Moreover, the manual operation may cause trauma, or introduce mechanical activation of the baroreceptors which may hinder the evaluation of the blood pressure responses to the electrical stimulation. Much of the long procedure time is spent waiting for stable baselines or return of blood pressure or heart rate values to pre-stimulation values.

SUMMARY

Various embodiments described relate to methods and systems that may be used to quickly find a candidate neural target for a neural stimulation therapy. For example, the method and systems may use an electrical tissue characteristic to identify an autonomic neural target, which does not require a procedure where time needs to be spent waiting for stable baselines or return of blood pressure or heart rate values to pre-stimulation values.

An example of a method may include moving at least one electrode to each of a plurality of tissue locations, measuring an electrical characteristic of tissue, using the at least one electrode, at each of the plurality of tissue locations, and analyzing the measured electrical characteristics to determine a neural target based on the comparison of the measurements of the electrical characteristic for tissue at the neural target relative to adjacent non-neural tissue. A graphical anatomic map may be created using the measurements. The neural target may be confirmed by delivering a stimulation through the at least one electrode used to measure the electrical characteristic, and monitoring a response to the stimulation. A neural stimulation therapy may be provided by delivering a therapeutic neural stimulation to the neural target using the at least one electrode used to measure the electrical characteristic.

An example of a system may include at least one electrode configured to be moved to each of a plurality of tissue locations, and a tissue tester configured to measure an electrical characteristic of tissue using the at least one electrode at each of the plurality of tissue locations. The tissue tester may be configured to analyze the measured electrical characteristics to determine a neural target based on the comparison of the measurements of the electrical characteristic for tissue at the neural target relative to adjacent non-neural tissue. The system may further include a graphical mapper configured to use the measured electrical characteristic of tissue at each of the plurality of tissue locations to create a graphical map of the neural target. The system may further be configured confirm the neural target by delivering stimulation through the at least one electrode used to measure the electrical characteristic. The system may further be configured to deliver a neural stimulation therapy by delivering therapeutic stimulation to the neural target by delivering therapeutic stimulation through the at least one electrode used to measure the electrical characteristic.

An example of a method for identifying a neural target may comprise placing a set of electrodes on tissue containing neural tissue where the set of electrodes including subsets of two or more electrodes. The method may further measure an electrical characteristic of tissue using the subsets within the set of electrodes placed on the tissue. The electrical characteristic of tissue may be used to quantify an ability of the tissue to oppose or to conduct an electric current or an ability of the tissue to transmit an electric field. The method may further compare measurements and identify a subset of electrodes that that provides a more desirable measurement of the electrical characteristic than other subsets of electrodes to identify the neural target. The more desirable measurement may be a measurement that has a lower ability to oppose the electric current, or a higher ability to conduct the electric current, or a higher ability to transmit an electric field.

An example of a method includes identifying a neural target, and applying a therapy to the neural target. Identifying the neural target may include placing a set of electrodes on tissue containing neural tissue, the set of electrodes including subsets of two or more electrodes, measuring an electrical characteristic of tissue using the subsets within the set of electrodes placed on the tissue, and comparing measurements of the electrical characteristic and identifying a subset of electrodes to identify the neural target based on the comparison of the measurements of the electrical characteristic for tissue at the neural target relative to adjacent non-neural tissue. The electrical characteristic of tissue may quantify an ability of the tissue to oppose or to conduct an electric current or an ability of the tissue to transmit an electric field.

An example of a system comprises a patch of electrodes for placement on tissue containing neural tissue, and a tissue tester configured to measure an electrical characteristic of tissue. The tissue tester may include a test controller and switches. The test controller and the switches may be configured to connect different combinations of the electrodes to create subsets of two or more electrodes to measure the electrical characteristic of tissue using the subsets. The test controller may be configured to measure an electrical characteristic of tissue using the subsets within the set of electrodes placed on the tissue, and compare measurements of the electrical characteristic and identify a neural target for a therapy based on the comparison of the measurements of the electrical characteristic for tissue at the neural target relative to adjacent non-neural tissue.

An example of a method for identifying a neural target on or near a heart may include measuring an electrical characteristic at a plurality of locations on or near the heart. Measuring the electrical characteristic may include compensating to reduce variations in the measured electrical characteristic caused by changes in cardiac activity. The method may further include analyzing the measured electrical characteristics to determine the neural target based on the comparison of the measurements of the electrical characteristic for tissue at the neural target relative to adjacent non-neural tissue.

An example of an ablation system may include an ablation catheter, a tissue tester, an ablation energy source and an ablation control. The ablation catheter may have electrodes, including electrodes configured to map tissue and electrodes configured ablate tissue. The tissue tester may be configured to measure an electrical characteristic of tissue. The tissue tester may include a test controller configured to measure an electrical characteristic of tissue on or near a heart using electrodes on the ablation catheter. The test controller may be configured to compensate to reduce variations in the measured electrical characteristic caused by changed in cardiac activity. The measured electrical characteristic is useful to identify a neural target for the ablation therapy based on the comparison of the measurements of the electrical characteristic for tissue at the neural target relative to adjacent non-neural tissue. The ablation energy source and the ablation control are configured to control an ablation procedure to ablate the identified neural target for the ablation therapy. This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
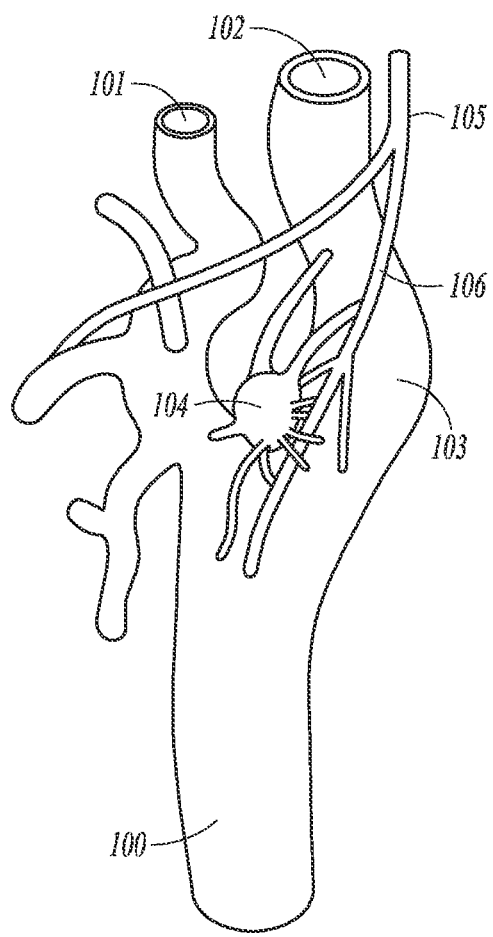
FIG. 1 illustrates, by way of example and not limitation, some neural tissue in a carotid sinus region.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Various embodiments of the present subject matter are able to quickly locate neural tissue. In some embodiments, for example, the process implemented may not require blood pressure measurements, but rather use an electrical characteristic of tissue related to an ability of the tissue to oppose or to conduct an electric current or an ability of the tissue to transmit an electric field to locate nerve fibers or nerve endings within tissue. Examples of such electrical characteristics include resistance, impedance or permittivity. For example, it has been found that permittivity and conductivity is higher in nerves than in skeletal muscle. E. Prokhorov Med. Biol. Eng. comput., 2002, 40, 323-326.

The ability to quickly locate neural tissue may be useful for mapping a carotid sinus region to find baroreceptor hotspots. It may be used to find other neural tissue as well, such as neural tissue in cardiac fat pads, tissue innervated by the renal nerve, the vagus nerve, the glossopharyngeal nerve, neural tissue near the pulmonary artery, etc. Carotid baroreceptors are terminal endings of the carotid sinus nerve-thus are nervous tissue. Baroreceptors lie within the adventitia of the carotid sinus, and can be accessed for stimulation from the luminal or ad luminal (intra-arterial) side. Measurements of a tissue characteristic or characteristics around the carotid sinus may be used to detect baroreceptor-rich areas in the carotid sinus or may be used to detect a high density of carotid sinus nerve fibers. By way of example, physically moving a mapping tool over the carotid sinus and taking impedance measurements may be used to determine locations with lower and higher impedance. Differences in these measurements may be used to determine the location of clusters of carotid baroreceptors. Some embodiments provide a tool with multiple electrodes spaced apart to optimize resolution of measurements. For example, the electrodes may be spaced within a range of 0.1 mm to 0.5 mm edge-to-edge. In an example where the measured electrical characteristic is impedance, an algorithm can be used to systematically and quickly locate areas of lower and higher impedance, which can be used to find locations of baroreceptors, carotid body, or carotid sinus nerve. An embodiment of the tool may be placed ad luminally, for example as a stent-like device with multiple electrodes. An embodiment of the tool may be advanced within the carotid artery.

The present subject matter may be used in a complementary manner with hemodynamic responses in locating the autonomic neural target on the carotid sinus. The present subject matter may be used as a stand-alone mapping system such as in cases where anesthesia blunts a baroreflex response to stimulation. A surgeon does not have to manually operate the mapping tool. Further, such "hands-free" mapping may prevent mechanical stimulation from biasing blood pressure responses during mapping Further, mapping may be done in areas that are not visible by dissection ("blind" mapping"), which improves the surgeon's opportunity to more fully map the region.

The mapping may not only provide a location but an orientation of the neural tissue, which may assist with placement of the permanent electrodes. For example, a bipolar electrode configuration maybe used to stimulate the neural target. If the neural target has a long axis, such as a nerve passing the target region or an elongated region of baroreceptors, then the bipolar stimulation electrodes may be orientated near this long axis to capture more neural tissue. Knowledge of the orientation of the neural tissue may be used to provide an effective algorithm that reduces the number of the regions of the tissue to be tested, resulting in a more efficient and faster process for mapping the tissue. For example, if one of the measurements of the electrical characteristic of tissue indicates that neural tissue is in that region, then electrode combinations may be tested parallel to or angled across the region. In one example, the neural target surrounds or courses along a blood vessel, and the tested electrode combinations are parallel to or angled across the blood vessel. Knowledge of the orientation of the blood vessel allows the algorithm for testing the electrical characteristic of tissue to follow the blood vessel where the neural tissue is expected to be found.

In some embodiments, for example, the algorithm may be configured to identify a boundary or boundaries between a region of neural tissue and a region of non-neural tissue. The algorithm may use the identified boundary or boundaries to determine where to take the next measurement(s) in order to continue to follow the boundary or boundaries of the neural tissue. The identified boundaries may be used to identify a region of the neural tissue to be further evaluated, and additional measurement may be made to map this region. Thus, the algorithm may iteratively determine region of interest based on the measurement results. Furthermore, different types of neural tissue (e.g. baroreceptor region, chemoreceptor region, nerve trunk) and different types of non-neural tissue (e.g. skeletal muscle, smooth muscle, cardiac muscle, cartilage, bone, fat, ligament, tendon etc.) may exhibit different electrical characteristics. These differences may be used to map these different types of tissue. Knowledge of typical physiology may be used to further discern the results of the tissue measurements.

By way of example and not limitation, the knowledge of the carotid sinus region may be used to help interpret the measurement results to identify baroreceptor regions, chemoreceptors, arterial tissue, the carotid sinus nerve and/or hypoglossal nerve. According to some embodiments, the algorithm may monitor the physiological parameter during the mapping process. The physiological parameter may be used to trigger a measurement (e.g. a measurement is taken during a certain phase of the respiration cycle or a certain phase of the cardiac cycle). The resulting measurement of the electrical characteristic of tissue may be stored, displayed and/or otherwise associated with the concurrent measurement of the physiological parameter. In an example, a respiratory cycle and/or cardiac cycle may be monitored, and at least some regions of the tissue may be measured through the cycle(s) to determine variances that may occur during the different phases of the respiratory cycle and/or cardiac cycle. As this is a more intensive process, the process may be implemented for only those regions that have been previously identified, based only on the measurements of electrical characteristics, as candidate therapeutic targets. In some embodiments, it can then be determined from these additional measurements of the candidate therapeutic targets which candidate therapeutic target is the most consistent candidate for the therapy throughout the different phases of the respiratory cycle and/or cardiac cycle. In some embodiments, the therapy may be timed to occur during a specific phase(s) of the respiratory cycle and/or cardiac cycle based on these additional measurements for a candidate therapeutic target.

Some embodiments are configured with the ability to take measurements at precisely the same time in the cardiac cycle and/or respiration cycle to eliminate noise or bias. Some embodiments are configured to compensate (e.g. subtract out) for changes in the measurement. For example, changes in impedance due to the pulsatility of the artery may be subtracted out. This may be particularly desirable in cases where the lead that is measuring impedance is in contact with the artery or otherwise in proximity to the blood within the artery. In some embodiments, the mapping tool may include another member that helps to align the electrode that is associated with a "hotspot" on the mapping tool with the electrode on the permanently implanted lead during fixation. In some embodiments, the mapping tool could be the permanent therapy lead.

The present subject matter may measure an electrical characteristic of tissue where the measurement may quantify an ability of the tissue to oppose or to conduct an electric current or an ability of the tissue to transmit an electric field. Those of ordinary skill in the art will understand that a measurement related to opposing current is inversely related to a measurement related to conducting electric current. By way of example, measurements for opposing (or conducting) current may include measurement for resistivity (or conductivity), measurements for resistance (or conductance), measurements for reactance (or susceptance), or measurements for impedance (or admittance). A measurement related to the ability of the tissue to transmit an electric field is permittivity. Electrical resistivity (also known as resistivity, specific electrical resistance, or volume resistivity) quantifies how strongly a given material opposes the flow of electric current. Electrical conductivity or specific conductance is the reciprocal of electrical resistivity, and measures a material's ability to conduct an electric current. Conductivity is defined as the inverse of resistivity. Admittance is defined as the inverse of impedance. Systems may be designed to measure such examples of tissue characteristics. Impedance is used herein as a specific example for measuring an electrical characteristic of tissue. Impedance is a complex quantity having a real part (i.e., resistance) and an imaginary part (i.e., reactance).). Impedance can be expressed as $Z=R+jX=|Z|\angle\theta$, where R is resistance, X is reactance, $|Z|$ is the magnitude and $\theta$ is the phase angle. In common practice, the magnitude is referred as impedance. However, any one or more of the four parameters can be used to detect a neural target. One can use either one parameter or a combination of parameters to improve the sensitivity of the nerve mapping and remove some the baseline noise.

By way of example, impedance measurements may be taken using unipolar or bipolar electrode arrangements. For unipolar, the impedance is measured between the small sensing electrode and a large reference electrode (which may be about 10 times larger in area) attached somewhere else such as patient chest. The impedance for unipolar measurement is mainly due to the tissue around the sensing electrode because of the geometry difference. The impedance measurement can be used to distinguish between the nerve and muscle tissue, given that they have very different impedances (e.g. about 100 times different) even though the baroreceptor tissue is 1 mm underneath. However, the unipolar measurement also includes the impedance from the measurement site to the reference electrode, which contributes to the impedance values and may act as a noise. If the baroreceptor region is about 1 $mm^2$ area and are about 1 mm underneath adventitia, the unipolar stimulation may use a unipolar electrode that has a dimension less than 1 mm×1 mm in cross section, such as 1 mm diameter circle. Larger electrode areas reduce the electrode sensitivity. For bipolar measurement, two electrodes are located next to each other on the probe. Bipolar is more efficient than unipolar due to the localization of the current field The electrode current flows between the two electrodes so only the tissue locate between the two electrodes are measured. This localized measurement can reduce the interference from body. However, a bipolar arrangement requires smaller electrodes. Given the dimension and location of the baroreceptor tissue, the bipolar arrangement may use a bipolar electrode pair that is about 1 to 2 mm apart with electrodes about 0.2 to 0.4 mm wide. If the nerves are located a little more deeper than the baroreceptors in the carotid sinus region, such as may be the case for nerves targeted for renal ablation, then bigger electrodes may be used. Impedance measurements of tissue in or near blood vessels may be taken intravascularly or extravasculary. Intravascular measurements may be more susceptible to bias or noise from the blood, and thus may use multiple measures of impedance to improve sensitivity.

A tissue region may be searched for a neural target by physically moving an electrode (e.g. unipolar configuration) or electrodes (e.g. bipolar configuration) over the tissue, and taking impedance measurements. Some embodiments may use the same electrode(s) used to take the impedance measurement to stimulate a potential neural target. For example, the potential neural target may be identified using measured impedance, and the neural target may be confirmed by stimulating the neural target and observing a physiological response to the stimulation, where the observed physiological response confirms that the neural target is stimulated. Some embodiments may sue the same electrode(s) used to take the impedance measurement to deliver neural stimulation to the neural target. For example, one neural target has been identified using the impedance measurement (and in some embodiments confirmed by delivering stimulation), the same electrode(s) may be fixed (e.g. sutured) in place and used to deliver the neural stimulation.

The frequency used to perform impedance mapping may be in a range between 5 kHz to 1000 kHz. Measurements using lower frequency measurement may encounter an electrode-electrolyte interface issue that can reduce detection sensitivity, and measurements using higher frequencies can have issue of cross-talk between wires that can reduce detection sensitivity. A single frequency may be used to measure impedance. However, it is also possible to use two or multiple frequencies and use the frequency dependency property to identify the nerve. For example, a type of tissue may be characterized by a relatively flat response or a relatively large between two frequencies. If impedance is measured at those two frequencies, then the tissue may be identified if the difference between those two frequencies matches the characteristic response of the tissue to the different stimulation frequencies.

The impedance measurements may be taken using two terminals or more than two terminals. For example, a two-terminal (sense and ground) measurement may be performed in the frequency range of 5 kHz to 1 MHz. The same electrodes may be used to inject current and measure voltage. A three-terminal system, by way of example and not limitation, may pass current through tissue using two electrodes and measure voltage using two electrodes, where one electrode is used to pass current through the tissue and also to measure voltage. For example, the three electrodes may be generally aligned with each other, and a distance between the electrodes used to pass current through the tissue may be larger than a distance of the electrodes to measure voltage. A four-terminal system, by way of example and not limitation, may include four electrodes that are generally aligned with each other. For example, the outside electrodes may be used to pass current through tissue and the inside electrodes may be used to measure voltage.

The autonomic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. The ANS may function in an involuntary, reflexive manner to regulate glands, to regulate muscles in the skin, eye, stomach, intestines and bladder, and to regulate cardiac muscle and the muscle around blood vessels, for example. The ANS includes, but is not limited to, the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system. The heart rate and force is increased when the sympathetic nervous system is stimulated, and is decreased when the sympathetic nervous system is inhibited and the parasympathetic nervous system is stimulated. Stimulating the sympathetic and parasympathetic nervous systems can have effects other than heart rate and blood pressure. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system and/or inhibiting the sympathetic nervous system constricts the pupil, increases saliva and mucus production, contracts the bronchial muscle, increases secretions and motility in the stomach and large intestine, and increases digestion in the small intention, increases urine secretion, and contracts the wall and relaxes the sphincter of the bladder. The functions associated with the sympathetic and parasympathetic nervous systems are many and can be complexly integrated with each other.

A pressoreceptive region or field is capable of sensing changes in pressure, such as changes in blood pressure. Pressoreceptor regions are referred to herein as baroreceptors. Baroreceptors are sensitive to the stretching of the wall that results from increased blood pressure from within, and function as the receptor of a central reflex mechanism that tends to reduce the pressure. Baroreflex functions as a negative feedback system, and relates to a reflex mechanism triggered by stimulation of a baroreceptor. Increased pressure stretches blood vessels, which in turn activates baroreceptors in the vessel walls. Activation of baroreceptors naturally occurs through internal pressure and stretching of the arterial wall, which excites the parasympathetic nervous system causing baroreflex inhibition of sympathetic nerve activity (SNA) and a reduction in systemic arterial pressure. An increase in baroreceptor activity induces a reduction of SNA, which reduces blood pressure by decreasing peripheral vascular resistance. Centrally mediated reflex pathways modulate cardiac rate, contractility and excitability.

Baroreflex is a reflex triggered by stimulation of a baroreceptor. Stimulating a baroreflex pathway and/or baroreceptors inhibits sympathetic nerve activity, stimulates the parasympathetic nervous system and reduces systemic arterial pressure by decreasing peripheral vascular resistance and cardiac contractility. Baroreceptor areas may be electrically stimulated to induce a baroreflex. As used herein, electrically stimulating a baroreceptor includes stimulating the nerve tissue including the nerve endings that innervate the baroreceptors. Stimulation of this nerve tissue near the baroreceptors causes neural signals to be sent to the central nervous system and induces a baroreflex response.

Baroreflex stimulation has been proposed for various therapies, including hypertension therapy and heart failure therapy. Hypertension is a cause of heart disease and other related cardiac co-morbidities. Hypertension occurs when blood vessels constrict. As a result, the heart works harder to maintain flow at a higher blood pressure, which can contribute to heart failure. Hypertension generally relates to high blood pressure, such as a transitory or sustained elevation of systemic arterial blood pressure to a level that is likely to induce cardiovascular damage or other adverse consequences. Hypertension has been defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease. Heart failure refers to a clinical syndrome in which cardiac function causes a below normal cardiac output that can fall below a level adequate to meet the metabolic demand of peripheral tissues. Heart failure may present itself as congestive heart failure (CHF) due to the accompanying venous and pulmonary congestion. Heart failure can be due to a variety of etiologies such as ischemic heart disease. Other therapies have been proposed as well, such as therapies to treat arrhythmias.

FIG. 1 illustrates, by way of example and not limitation, some neural tissue in a carotid sinus region. The illustrated physiologic structure shows the bifurcation of carotid artery, illustrating the common carotid artery 100 into an external carotid artery 101, and an internal carotid artery 102. The carotid sinus 103 is a dilated area in the bifurcation which includes many baroreceptors. Baroreceptor distribution may vary from person-to-person. However, baroreceptors appear to be more highly concentrated near the bifurcation of the interior carotid artery and external carotid artery off of the common carotid artery. Thus, some embodiments provide an orientation to stimulate the tissue area with the high concentration of baroreceptors. The carotid body 104 is located near the bifurcation and includes a cluster of chemoreceptors. FIG. 1 also illustrates nerves that innervate the region, including the glossopharyngeal nerve 105 which branches into the carotid sinus nerve 106. As provided above, baroreceptors are sensitive to changes in blood pressure. The chemoreceptors in the carotid body are sensitive to blood gas concentrations, primarily reductions in $O_2$ partial pressure. Both the baroreceptors and the chemoreceptors relay information to the central nervous system. However, eliciting nerve traffic in neural pathways from baroreceptors can have a parasympathetic effect where their stimulation mimics the sensing of higher blood pressure causing the central nervous system to lower heart rate and blood pressure; whereas eliciting nerve traffic in neural pathways from chemoreceptors can have a sympathetic effect where their stimulation mimics a reduction in $O_2$ causing the central nervous system to raise heart rate and blood pressure. Mapping this region may be useful to target some neural tissue and avoid other neural tissue. For example, a baroreflex stimulation therapy may target neural tissue with a high concentration of baroreceptors, and avoid he chemoreceptors in the carotid body. It has been proposed to ablate neural tissue in the carotid body to treat hypertension. Such an ablation therapy may target neural tissue with chemoreceptors and avoid neural tissue with baroreceptors.

Figure 2:
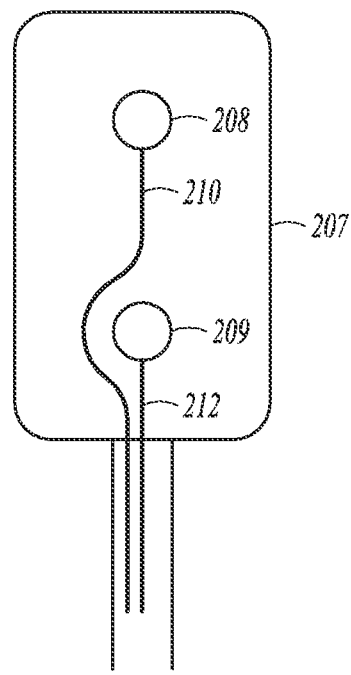
FIGS. 2-4 illustrate lead examples with more than one electrode that can be used to map a tissue region to identify a neural target within the tissue region.
Figure 3:
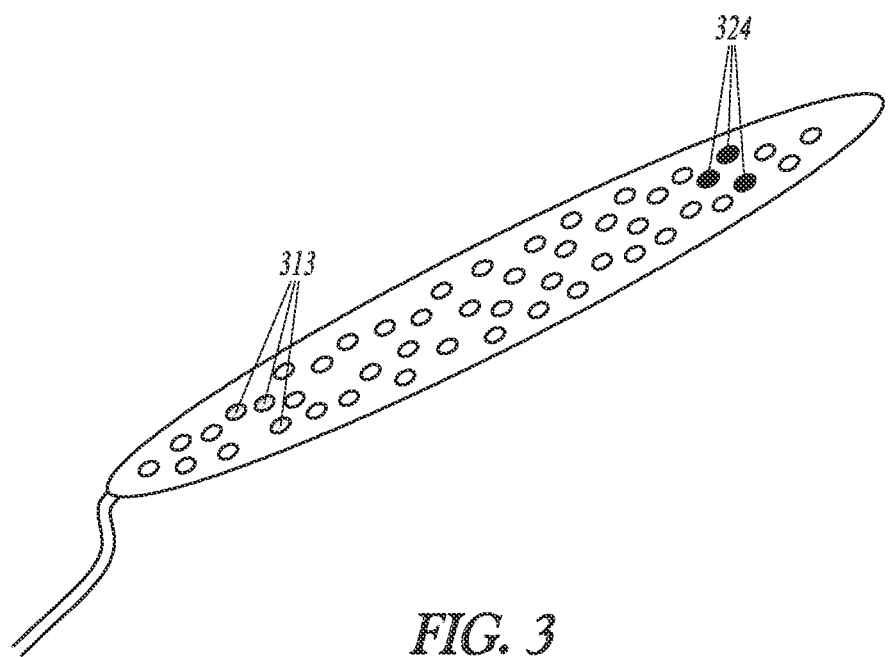
Figure 4:
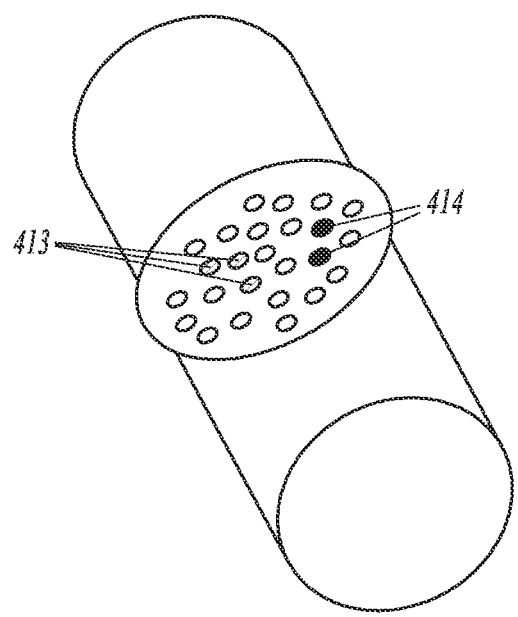

FIGS. 2-4 illustrate lead examples with more than one electrode that can be used to map a tissue region to identify a neural target within the tissue region. FIG. 2 illustrates a lead 207 that includes at least two electrodes 208 and 209, each connected by a conductor 210 211 to a pulse generator (not shown). The electrodes 208 and 209 can be used to deliver an electrical stimulus to tissue for use in measuring the electrical characteristic of the tissue. A surgeon may manually move the lead, quickly measuring the electrical characteristic of tissue in multiple locations, to map a region of tissue to locate neural tissue. The measurement of the electrical characteristic may be displayed or otherwise communicated to user(s) of the system. The measurements may be automatically recorded. Differences in these measurements may be used to determine the location of neural tissue. Some embodiments, as generally illustrated by the example in FIG. 3, provide a tool with multiple electrodes spaced apart to optimize resolution of measurement. The electrodes may have an edge-to-edge spacing within a range of about 0.1-0.5 mm edge to edge, for example. An embodiment of the tool may be placed ad luminally, for example as a stent-like device with multiple electrodes. An embodiment of the tool may be advanced within the carotid artery. An example of a stent-like tool is illustrated in FIG. 4. For example, where the measured electrical characteristic is impedance, an algorithm can be used to systematically and quickly locate areas of lower and higher impedance, which can be used to find locations of baroreceptors, carotid body, or carotid sinus nerve. Although the measured tissue characteristic is dependent on the electric current or field extending between or among two or more electrodes, the electrode location may be used to identify the candidate target tissue. By way of example and not limitation, the electrodes can be characterized as corresponding an area of lower impedance (e.g. 313, 413), higher impedance (314, 414), and intermediate impedance (not shown for clarity). The areas of lower impedance (e.g. 313, 413) indicate the presence of more neural tissue.

The electrodes may be placed on a side of a patch. The patch may be constructed of material that may be implanted within the patient and may be sutured or otherwise attached to tissue near the carotid sinus. The patch may be pliable, allowing the patch to generally conform to the surface of the tissue to which it is attached. The patch may act as a shield to keep electrical stimulation fields on the electrode side of patch. Each electrode may be connected to a respective wire, which allows any of the electrodes to be selectively used in delivering the bipolar stimulation to tissue in the carotid sinus. Each wire may extend from the electrode near a distal end of the lead toward a proximal end of the lead. In some embodiments, a multiplexor may be used near the distal end of the lead so that fewer conductors need be used in the lead. In some embodiments, some of the electrodes may be electrically connected together (e.g. hard wired) which also would also only require fewer wires in the lead. It is noted that these electrode patterns are examples, and are not intended to be exclusive examples. Rather, a bipolar stimulation configuration can be selected to use a selected one or more of the electrodes as a cathode. In some embodiments, the bipolar stimulation configuration can be selected to use a selected one or more of the electrodes as an anode.

Figure 5:
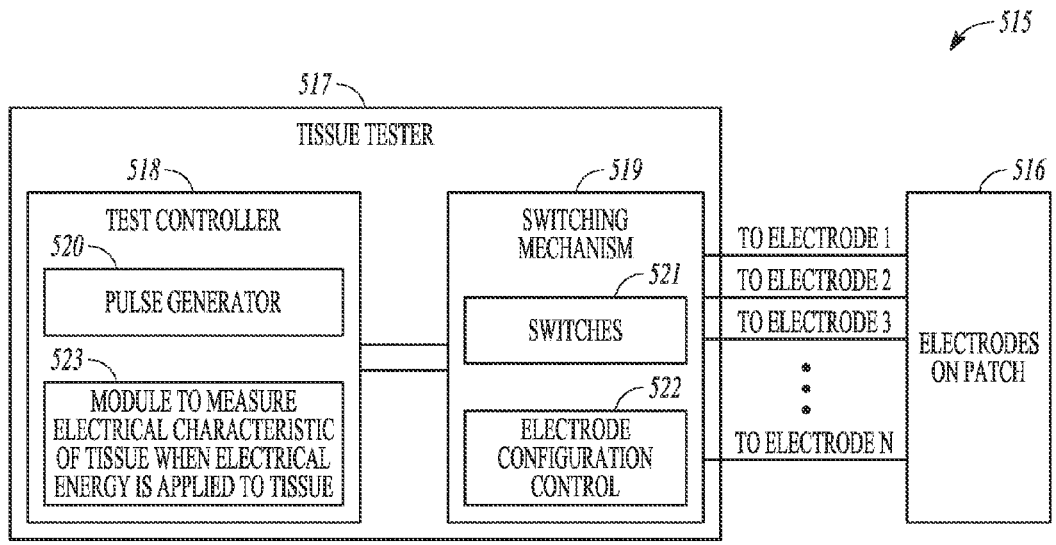
FIG. 5 illustrates an example of a system capable of mapping a tissue region by forming various electrode combinations, and using the formed electrode combinations to deliver electrical energy to the tissue region and measure an electrical characteristic of the tissue.

FIG. 5 illustrates an example of a system capable of mapping a tissue region by forming various electrode combinations, and using the formed electrode combinations to deliver electrical energy to the tissue region and measure an electrical characteristic of the tissue. The illustrated system 515 may include electrode(s) on a patch 516, such as illustrated in FIGS. 2-4 or such another patch with one electrode (e.g. used for a unipolar configuration), two electrodes or more than two electrodes. The system 515 also includes a tissue tester 517 with a test controller 518 and a switching mechanism 519 configured to connect electrode(s) to the test controller 518. The test controller 518, as illustrated in FIG. 5, may include a pulse generator 520 configured to deliver electrical neural stimulation using two conductors. The switching mechanism 519 includes switches 521 and an electrode configuration control 522 that may be configured to control the switches to select the electrode(s) to function as the anode and the electrode(s) to function as the cathode for bipolar stimulation. The illustrated test controller 518, as illustrated in FIG. 5, may also include a module 523 configured to measure an electrical characteristic (or characteristics) of tissue when electrical energy is applied to the tissue. By way of example and not limitation, the measured electrical characteristic may be resistance, impedance or permittivity.

Figure 6:
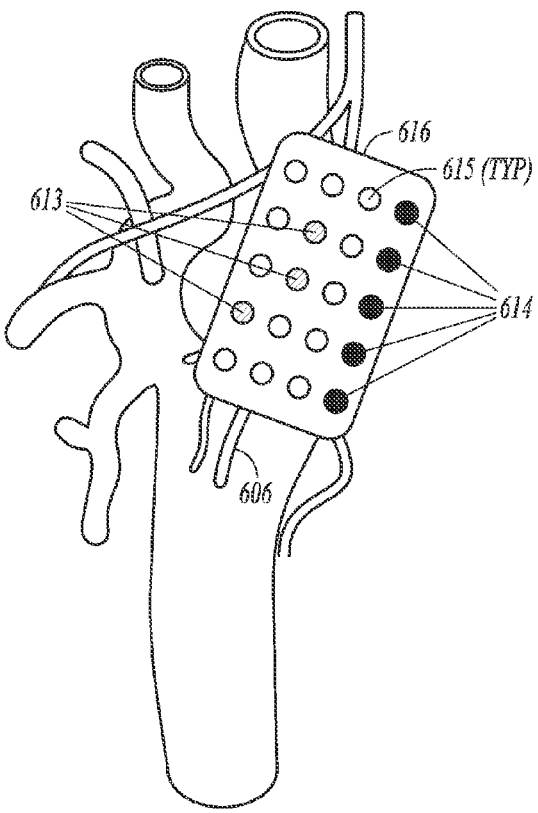
FIG. 6 illustrates a patch with mapping electrodes over the carotid sinus.

FIG. 6 illustrates a patch with mapping electrodes over the carotid sinus region that was illustrated in FIG. 1. Some embodiments provide a tool or patch 616 with multiple electrodes spaced apart to optimize resolution of measurement. The electrodes may have an edge-to-edge spacing within a range of about 0.1-0.5 mm edge to edge, for example. For example, where the measured electrical characteristic is impedance, an algorithm can be used to systematically and quickly locate areas of lower and higher impedance, which can be used to find baroreceptors, a carotid body, or a carotid sinus nerve. By way of example and not limitation, each of these electrodes can be characterized has being located in an area of lower impedance (e.g. 613), higher impedance (e.g. 614), and intermediate impedance (e.g. 615). The areas of lower impedance may indicate the presence of more neural tissue (e.g. a carotid sinus nerve 606 or a more dense area of baroreceptors) in those areas of the tissue. The areas of intermediate impedance may indicate the presence of less densely populated baroreceptors in those areas of the tissue. The areas of high impedance may indicate that little or no neural tissue is found in those areas of the tissue.

Figure 7:
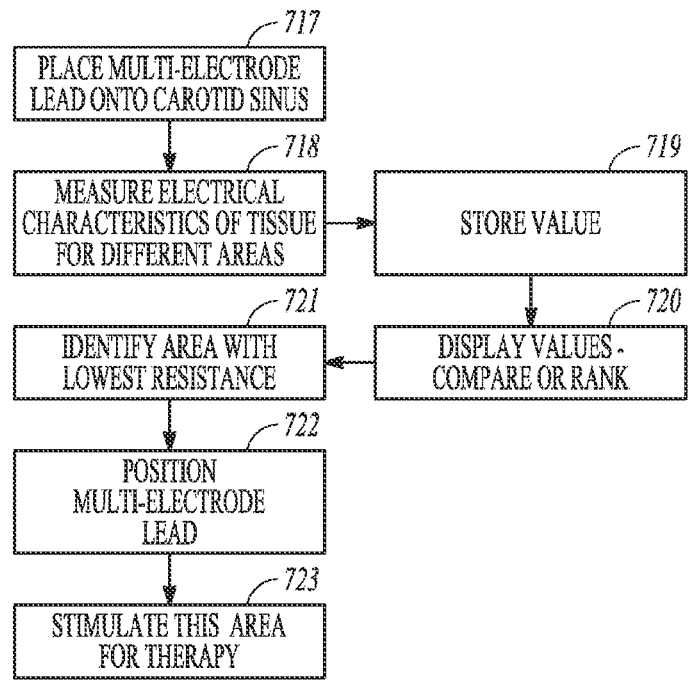
FIG. 7 illustrates an example of a method for identifying an autonomic target for therapy within a tissue region using an electrical characteristic of tissue and delivering the therapy to the autonomic target.

FIG. 7 illustrates an example of a method for identifying an autonomic target for therapy within a tissue region using an electrical characteristic of tissue and delivering the therapy to the autonomic target. A multi-electrode lead may be placed onto a carotid sinus tissue region, as illustrated at 717. At 718 an electrical characteristic of the tissue region is measured for a number of different areas in the tissue. By way of example and not limitation, resistance or impedance may be measured. The values for the measured electrical characteristic may be stored at 719, and displayed, compared and/or ranked at 720. A user may select the target based on the display information. The selected area may be based on the best ranking (e.g. lowest impedance or highest conductance) or may be based on some other criteria (e.g. top 25%, or bottom 25% or within a range such as 40% to 60%). The area of the tissue with the most desirable value for the electrical characteristic (e.g. lowest resistance or highest conductance) is identified at 721. There may be circumstances where it is desired to target an area with neural tissue, but not the area with the most neural tissue. For example, it may not be desired to ablate the area with the most neural tissue, but rather to ablate the area with less neural tissue to cause the effect to be more incremental to avoid over-ablation. After identifying the area with the most desirable value, the multi-electrode lead may be positioned at 722 to stimulate this area, and this area may be stimulated at 723.

Figure 8:
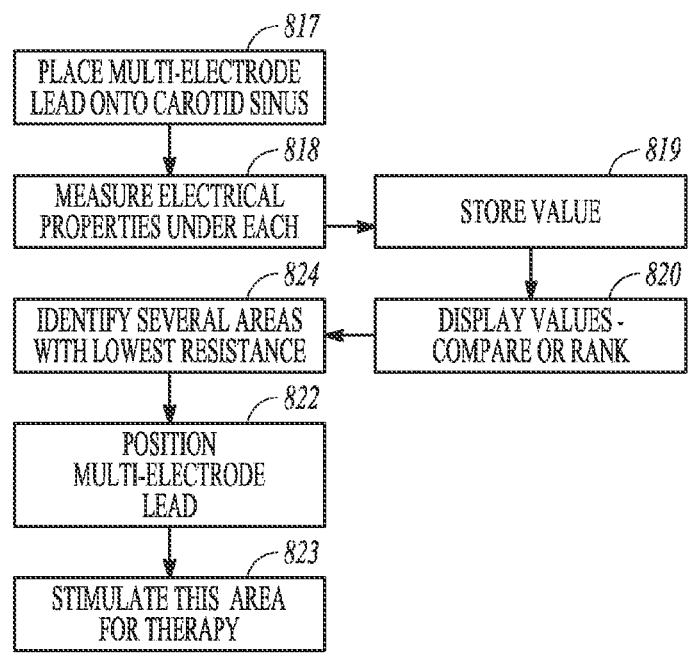
FIG. 8 illustrates an example of a method for identifying autonomic targets for therapy within a tissue region using an electrical characteristic of tissue and delivering the therapy to the autonomic targets.

FIG. 8 illustrates an example of a method for identifying autonomic targets for therapy within a tissue region using an electrical characteristic of tissue and delivering the therapy to the autonomic targets. The example illustrated is FIG. 8 has similarities to the example illustrated in FIG. 7, with an exception that several areas with desirable values are found, and the stimulation is applied to these desirable areas. For example, there may be more than one region of high baroreceptor density. In particular a multi-electrode lead may be placed onto a carotid sinus tissue region, as illustrated at 817. At 818 an electrical characteristic of the tissue region is measured for a number of different areas in the tissue. By way of example, resistance or impedance may be measured. The values for the measured electrical characteristic may be stored at 819, and displayed, compared and/or ranked at 820. Several areas of the tissue with a desirable value for the electrical characteristic (e.g. lowest resistance) are identified at 824. After identifying the area with the most desirable value, the multi-electrode lead may be positioned at 822 to stimulate these areas, and these areas may be stimulated at 823.

Figure 9:
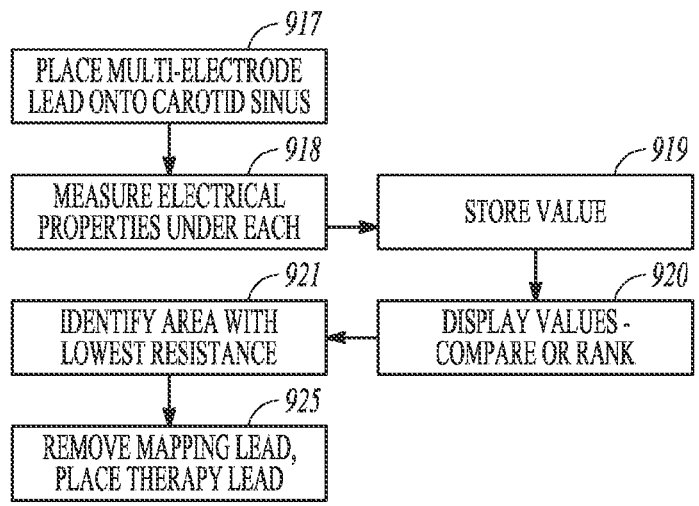
FIG. 9 illustrates an example of a method for using a mapping lead to identify autonomic targets for therapy within a tissue region using an electrical characteristic of tissue and using a therapy lead to deliver the therapy to the autonomic targets.

FIG. 9 illustrates an example of a method for using a mapping lead to identify autonomic targets for therapy within a tissue region using an electrical characteristic of tissue and using a therapy lead to deliver the therapy to the autonomic targets. The example illustrated is FIG. 9 has similarities to the example illustrated in FIG. 7, with an exception that the lead to deliver the therapy is different than the lead used to map the tissue region. In particular a multi-electrode lead may be placed onto a carotid sinus tissue region, as illustrated at 917. This lead may be referred to as a mapping lead. At 918 an electrical characteristic of the tissue region is measured for a number of different areas in the tissue. By way of example, resistance or impedance may be measured. The values for the measured electrical characteristic may be stored at 919 and displayed, compared and/or ranked at 920. The area of the tissue with the most desirable value for the electrical characteristic (e.g. lowest resistance) is identified at 925, the location may be marked, the mapping lead removed and a therapy lead can be placed, using the marked tissue, to stimulate the area of tissue with the most desirable value. The tissue may be physically marked or may be virtually marked using an anatomical mapping system. The anatomical mapping system may provide a graphical representation of the tissue based on the measurements of the electrical characteristics of tissue.

Figure 10:
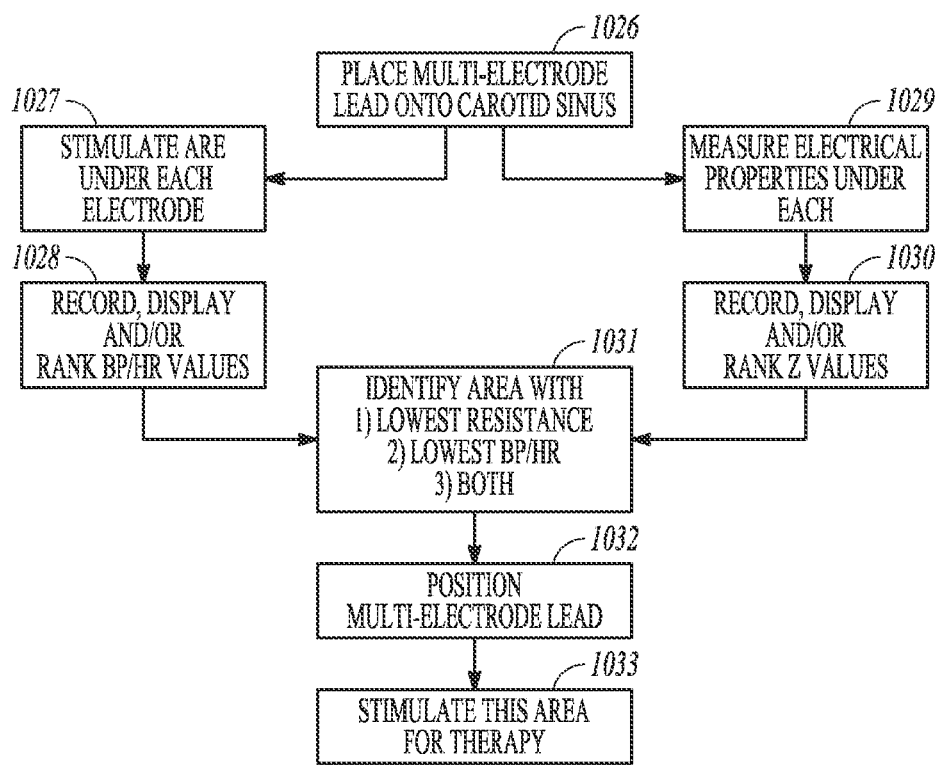
FIG. 10 illustrates an example of a method for identifying an autonomic target for therapy within a tissue region using a combination of an electrical characteristic of tissue and an autonomic response to stimulation, and delivering the therapy to the autonomic target.

FIG. 10 illustrates an example of a method for identifying an autonomic target for therapy within a tissue region using a combination of an electrical characteristic of tissue and an autonomic response to stimulation, and delivering the therapy to the autonomic target. A multi-electrode lead may be placed onto a carotid sinus tissue region, as illustrated at 1026. At 1027 the tissue is stimulated in a number of areas using a number of different combinations of electrodes. At 1028 a physiological parameter, such as blood pressure, heart rate or other physiological response to autonomic stimulation, may be recorded, displayed compared and/or ranked. At 1029 an electrical characteristic of the tissue region is measured for a number of different areas in the tissue. By way of example, resistance or impedance may be measured. The values for the measured electrical characteristic may be recorded, displayed, compared and/or ranked at 1030. At 1031 the target area for stimulation is identified. This may be based on the measured characteristic (e.g. lowest resistance), or the physiological parameter (e.g. blood pressure or heart rate), or both. The location may be marked (e.g. physically or virtually), the mapping lead removed and a therapy lead can be placed, using the marked tissue, to stimulate the area of tissue with the most desirable value; or the multi-electrode lead may be used to deliver therapy using select electrodes on the multi-electrode lead 1032. The selected area is stimulated for the therapy 1033.

Figure 11:
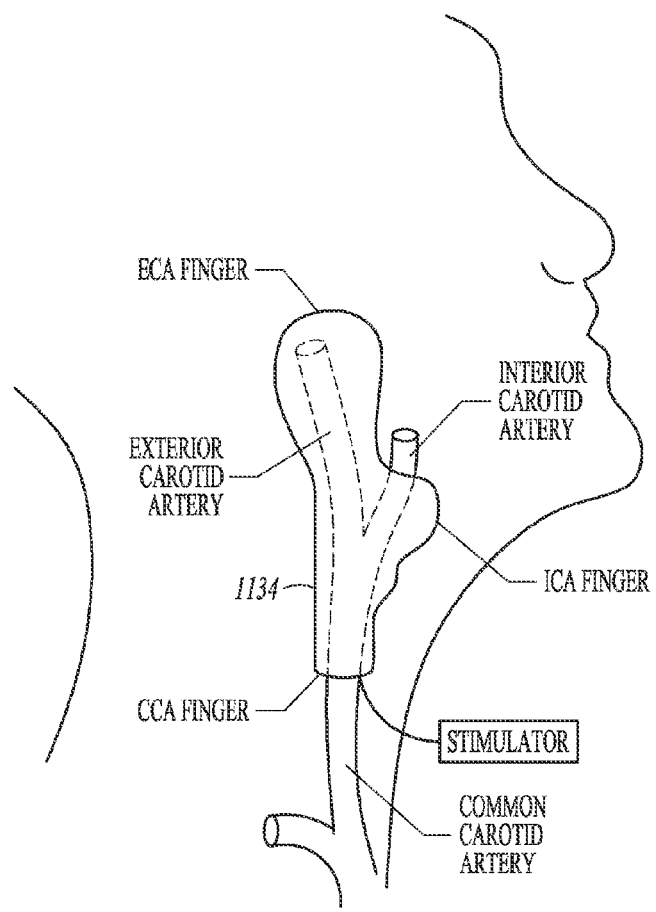
FIG. 11 illustrates, by way of example and not limitation, an embodiment electrode patch placed over the carotid sinus region.

FIG. 11 illustrates, by way of example and not limitation, an embodiment electrode patch placed over the carotid sinus region. The patch 1134 may have protrusions, which may be referred to as fingers. A CCA finger runs along the common carotid artery, an ICA finger runs along the interior carotid artery, and the ECA finger runs along the exterior carotid artery. The length of the patch from the CCA edge to the ECA edge may be within a range of about 2 cm to about 4 cm, and the length of the ICA finger of the patch may be within a range of about 0.5 cm to about 2 cm. The width of the ECA finger may be about 0.5 cm to about 1 cm, the width of the ICA finger may be about 0.5 cm to about 1.5 cm. In some embodiments, the distance between electrodes may be within a range of about 0.5 mm to 2 mm edge to edge.

Figure 12:
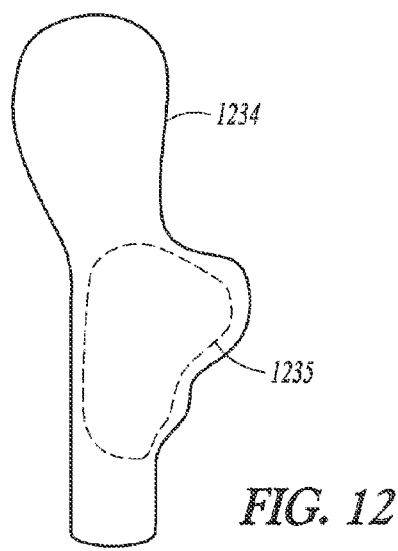
FIG. 12 illustrates, by way of example and not limitation, an example of a carotid sinus patch with a mapping electrode region

FIG. 12 illustrates, by way of example and not limitation, an example of a carotid sinus patch with a mapping electrode region. The mapping region 1235 of the patch 1234 can include a number of electrodes configured to measure the electrical characteristic of tissue. Modeling information suggests that it is the tissue directly under the cathode that gets the greatest amount of energy. Thus, locating the cathode of the stimulation near a baroreceptor hotspot is desirable. U.S. Provisional Patent Application 61/836,431 filed on Jun. 18, 2013 and entitled System and Method for Mapping Baroreceptors relates to mapping a baroreceptor region and position a cathode on a baroreceptor hotspot. U.S. Provisional Patent Application 61/836,431 is incorporated by reference herein in its entirety. The location of the anode appears to be less significant, and can be positioned away from potential cathodes for the stimulation configuration. Therefore, electrodes in the mapping region may be configured to be potential cathodes, and the anode may be on the ECA finger.

Figure 13:
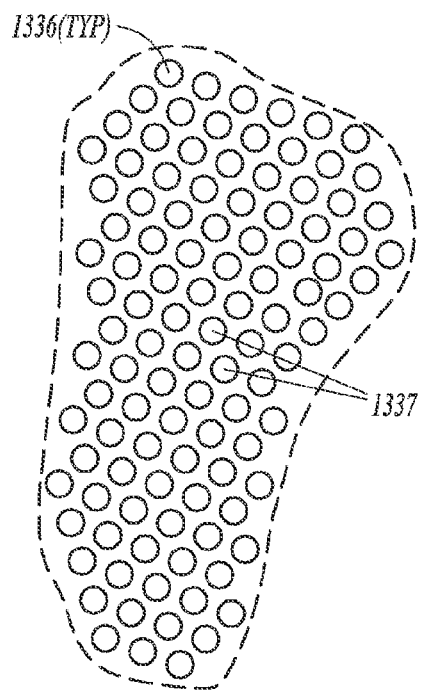
FIG. 13 illustrates, by way of example and not limitation, a plurality of mapping electrodes such as may be positioned within a mapping electrode region or a portion thereof.

FIG. 13 illustrates, by way of example and not limitation, a plurality of mapping electrodes such as may be positioned within a mapping electrode region or a portion thereof, such as the mapping electrode region 1235 illustrated in FIG. 12. This drawing was not intended to be drawn to scale, but was rather intended to illustrate that many electrodes 1336 may be distributed across the area to be tested. For example, the impedance or resistance may be tested between adjacent electrodes. In some embodiments, the mapping electrodes have the same contact area with the tissue, and the distance between adjacent electrodes is relatively the same so that the amount of tissue that the current flows through is about the same regardless of the electrodes that are tested. For example, assuming that the tissue has the same conductivity throughout, the tissue between electrodes having a shorter current path through the tissue will have lower resistance than the tissue between electrodes having a longer current path. By using equidistant or relatively equidistant electrodes to test the tissue, there is more confidence that changes in the tissue characteristic between adjacent electrodes is attributable to the neural tissue rather than to the distance between electrodes. In other embodiments, the system may be programmed with the known distances between electrodes. It may be assumed, for example, that the area of the current distribution through the tissue is relatively constant. The system can than normalize the measure of the tissue characteristic to account for differences in the current path. For example, a measure of resistance may be divided by the distance to obtain a measure that is proportional to resistivity of the tissue, which can then be compared to other measures of resistivity. By way of example, it may be determined that electrodes 1337 have a desirable measure of a tissue characteristic (e.g. a low tissue resistance).

In some embodiments, the tissue in the region may be marked (e.g. physically marked or virtually marked) to identify the location of these electrodes when the desirable measure was obtained. For example, the patch may have small apertures in which the physician can physically mark the tissue through the apertures. The marking may simply indicate a location of neural target or the marking may indicate both a location but also an orientation of the neural target such as may be desirable if a nerve passes through the area or if a baroreceptor region has a footprint with a long axis. Bipolar stimulation electrodes may be positioned to deliver the stimulation along this long axis. The tissue may be virtually marked using an anatomical mapping system. The anatomical mapping system may provide a graphical representation of the tissue based on the measurements of the electrical characteristics of tissue. Some examples of such anatomical mapping systems that provide representations of tissues based on a physiological measurement to generate coordinates include: U.S. Pat. No. 7,477,763 entitled "Computer Generated Representation of the Imaging Pattern of an Imaging Device," U.S. Pat. No. 7,633,502 entitled "System and Method for Graphically Representing Anatomical Orifices and Vessels," U.S. Pat. No. 7,610,078 entitled "System and Method of Graphically Generating Anatomical Structures Using Ultrasound Echo Information." These patents were assigned to Boston Scientific Scimed. Inc. U.S. Pat. Nos. 7,477,763, 7,633,502, and 7,610,078 are herein incorporated by reference in their entirety.

Figure 14:
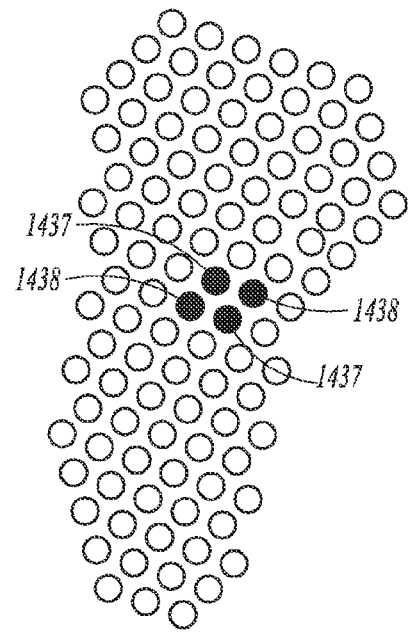
FIG. 14 illustrates an example of a mapping electrode region, or a portion thereof, with mapping electrodes grouped together function as a stimulation electrode such as a cathode.

In some embodiments, some of the mapping electrodes can be converted to provide a greater area for use as a cathode for the neural stimulation therapy. FIG. 14 illustrates an example of a mapping electrode region, or a portion thereof, such as the mapping electrode region 1235 illustrated in FIG. 12 with mapping electrodes grouped together to function as a stimulation electrode such as a cathode 1438. The patch may be sutured in place or otherwise attached before the testing begins. The electrodes 1437 with which the desired tissue measurement was found can be combined with some adjacent electrodes 1438 to function as a cathode. The anode may be positioned elsewhere on the patch. In some embodiments, some of the mapping electrodes may be configured to provide the anode, which may allow the stimulation current to flow in relative alignment with the orientation of the neural target.

Figure 15:
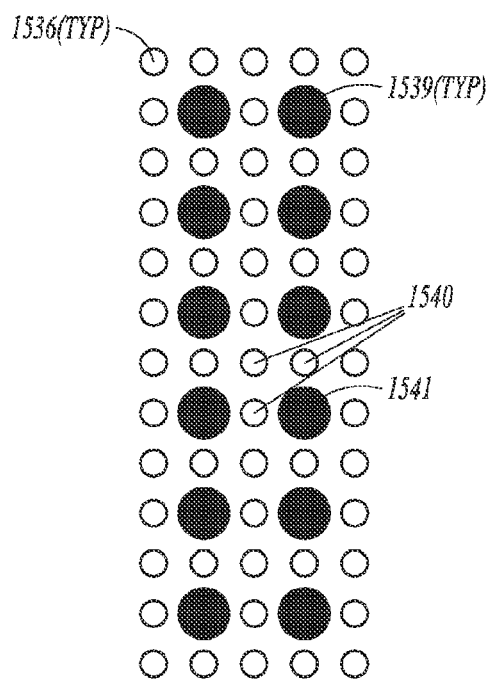
FIG. 15 illustrates an example of a mapping electrode region, or a portion thereof, with stimulation electrodes (e.g. cathodes) interspersed within the mapping electrodes.

FIG. 15 illustrates an example of a mapping electrode region, or a portion thereof, with stimulation electrodes 1539 (e.g. cathodes and/or anodes) interspersed within the mapping electrodes 1536. The patch may be sutured in place before the testing begins. For example, a desired tissue measurement may have been found with electrodes 1540. The system may then select, either automatically or with input from a user, a stimulation electrode 1541 that is close to the electrodes 1540.

Figure 16:
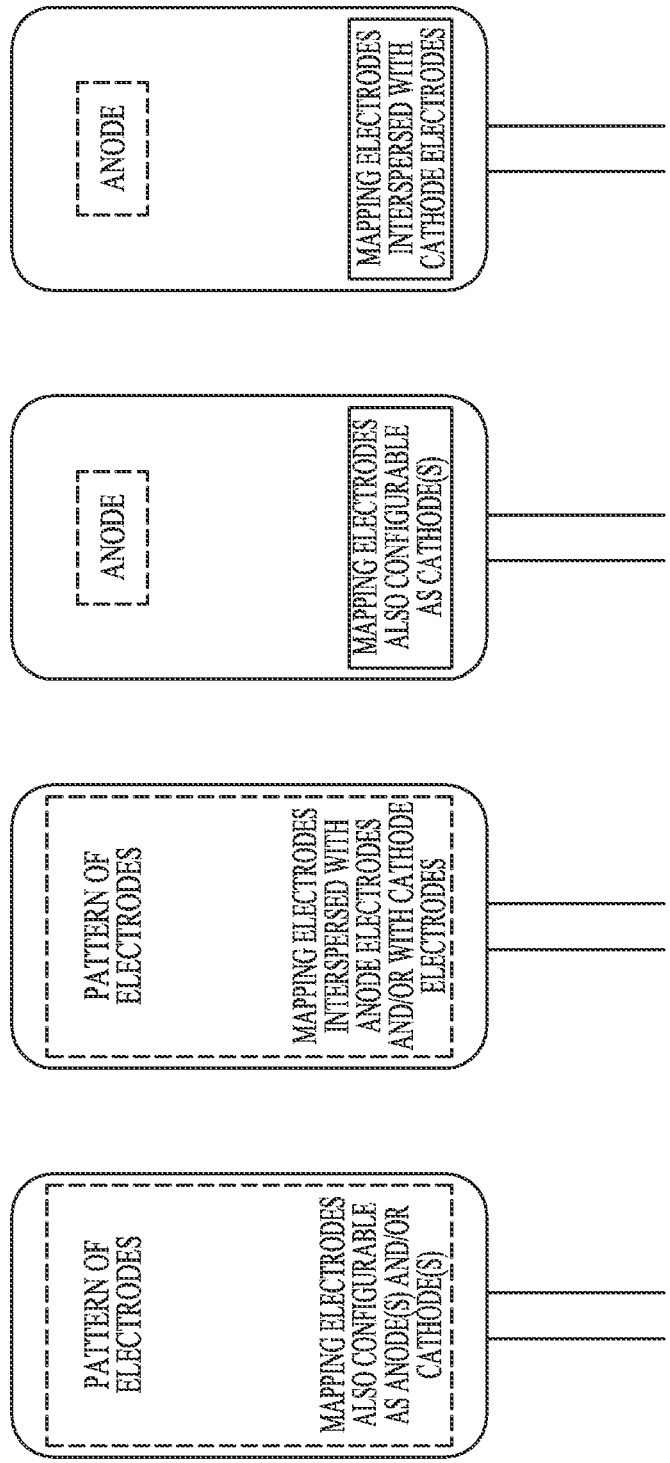
FIGS. 16A-16D illustrate, by way of example and not limitation, electrode pattern examples and potential electrode configurations.

FIGS. 16A-16D illustrate, by way of example and not limitation, electrode pattern examples and potential electrode configurations. In FIG. 16A, for example, the patch may include a pattern of mapping electrodes. Any of the mapping electrodes may be configured for use as an anode or as a cathode. The mapping electrodes may be combined with other mapping electrodes to provide a desired surface area for the anode or cathode. This example is similar to the embodiment illustrated in FIG. 14. In FIG. 16B, for example the patch may include a pattern of mapping electrodes interspersed with anode electrode(s) and/or cathode electrode(s). The results of the mapping process will identify a neural target, and the electrode(s) (e.g. cathode) may be selected that are near the neural target. This example is similar to the embodiment illustrated in FIG. 15. FIGS. 16C and 16D are similar to FIGS. 16A and 16B, respectively, except that the anode or anodes are separated from the mapping electrodes. The mapping electrodes are used to determine the desired location of the cathode(s). Two or more mapping electrodes may be used to function as a cathode for the stimulation as illustrated in FIG. 16C, or one or more cathode electrodes interspersed within the mapping electrodes may be selected to function as the cathode for the stimulation as illustrated in FIG. 16D.

Figure 17:
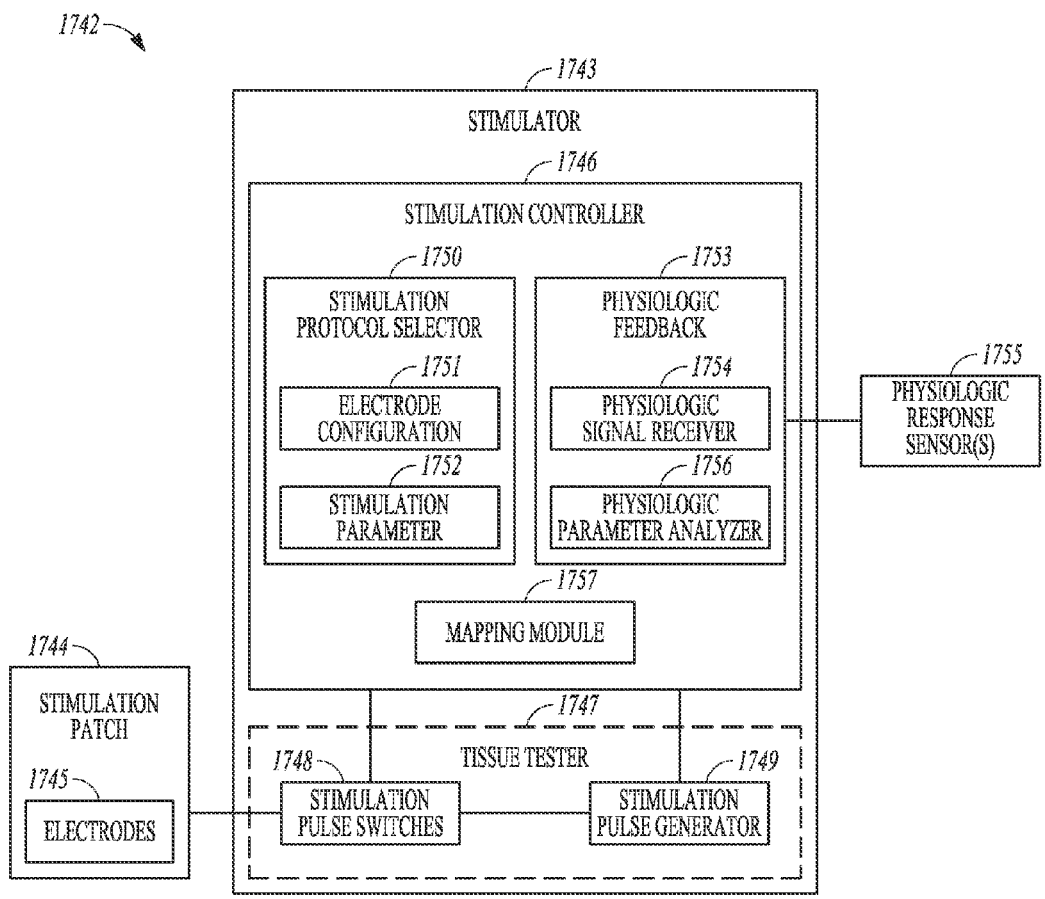
FIG. 17 illustrates, by way of example and not limitation, an embodiment of a system for mapping an autonomic neural target.
Figure 18:
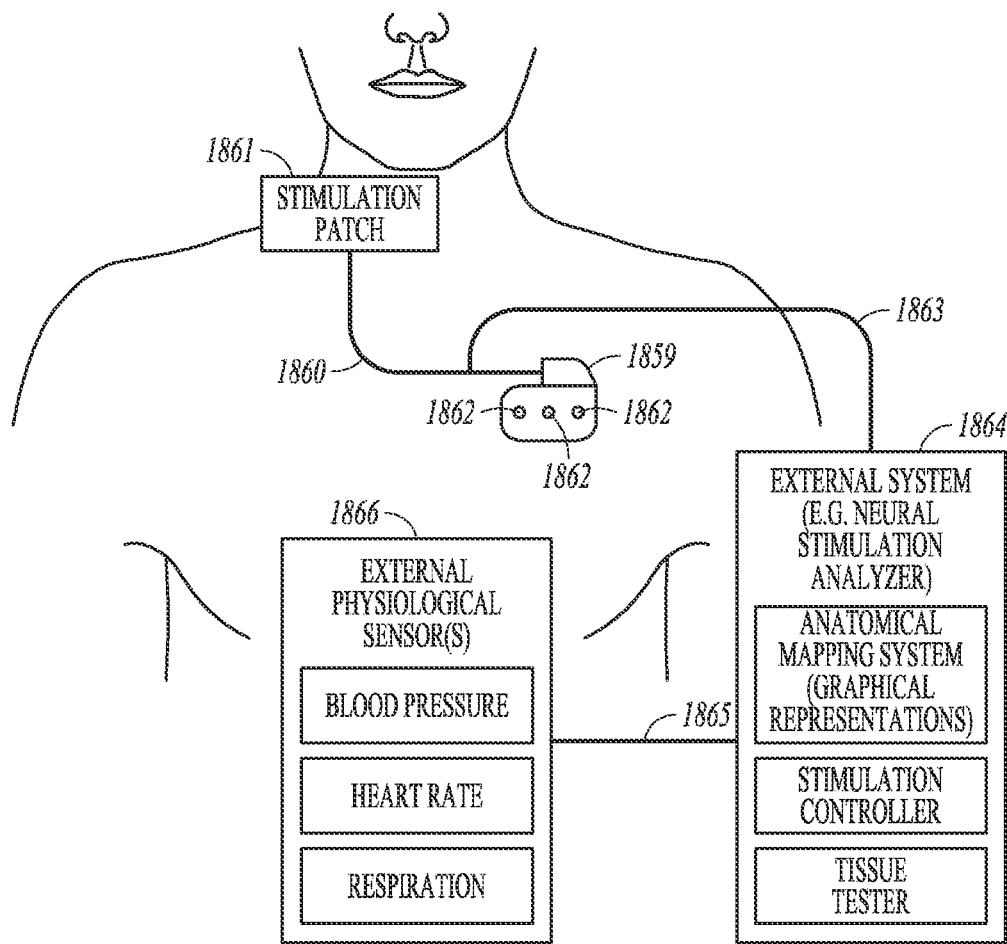
FIG. 18 illustrates, by way of example and not limitation, an implantable neural stimulator and an embodiment of an external system such as a neural stimulation system analyzer.

FIG. 17 illustrates, by way of example and not limitation, an embodiment of a system for mapping an autonomic neural target. For example, the system may be used to map a baroreflex system. The illustrated system 1742 includes a stimulator 1743 and a stimulation patch 1744 with electrodes 1745 that may be configured to deliver electrical energy to the tissue of the patient. The illustrated stimulator 1743 may include a stimulation controller 1746 and a tissue tester 1747. The tissue tester 1747 may include a module of switches 1748, and a stimulation pulse generator 1749. The switches 1748 selectively connect lead conductors 1750 to connect electrodes 1745 to the pulse generator 1749. The illustrated controller 1746 may include a stimulation protocol selector 1750. The stimulation protocol selector 1750 may include an electrode configuration selector 1751, which may work with the module of switches 1748 to control switching. The stimulation protocol selector 1750 may also include a stimulation parameter selector 1752 which may work with the stimulation pulse generator to control the parameters of the neural stimulation. Examples of such parameters include the amplitude, pulse width, pulse frequency, burst duration, burst frequency, or other start/stop parameters of the stimulation. The controller may also include a physiologic feedback module 1753. The physiologic feedback module 1753 may include a physiologic signal receiver 1754 to receive signal(s) from physiologic response sensor(s) 1755, and a physiologic parameter analyzer 1756 configured to analyze the received signal to provide feedback used to control the stimulation. The stimulation controller 1746 may also include a mapping module 1757 used to control a mapping process and store the results from the mapping. FIG. 18 illustrates, by way of example and not limitation, an implantable neural stimulator and an embodiment of an external system such as a neural stimulation system analyzer. The illustrated implantable neural stimulator 1859 is placed subcutaneously or submuscularly in a patient's chest with a lead 1860 positioned to stimulate baroreceptors in a carotid sinus region. The lead may include a stimulation patch 1861 with a plurality of electrodes. The illustrated system provides a lead to the right carotid sinus region. The lead could be routed to the left carotid sinus region. Some embodiments may use leads to stimulate both the left and right carotid sinus regions. The neural stimulator may include leadless ECG electrodes 1862 on the housing of the device, which are capable of being used to detect heart rate, for example, to provide feedback for the neural stimulation therapy. At the time of the implantation of the neural stimulator, a test lead cable 1863 may be temporarily connected to the implanted neural stimulation lead 1860 to enable a neural stimulation system analyzer 1864 to determine an appropriate placement of the lead, and verify the integrity of the stimulation path within the lead. Sensor cable(s) 1865 connect the external system 1864 to external physiology sensors 1866. These sensor(s) are used by the analyzer to detect an autonomic response to the neural stimulation. For example, heart rate, blood pressure, or respiration may be sensed to detect a baroreflex response. The external system 1864 may include a stimulation controller and tissue tester similar to the stimulator 1743 illustrated in FIG. 17. The external system 1864 may include an anatomical mapping system configured to provide graphical representations of the anatomy based on the measured electrical characteristics of the tissue. These graphical representations may also, in some examples, be based on monitored physiological responses, such as from external physiological sensor(s) 1866 or other sensors. The graphical representations may also account for represent the cardiac cycle and/or respiratory cycle during the measurements. The anatomical mapping system may be used to virtually mark the tissue to identify a therapeutic target. Thus, the external system 1864 may be used to map the region to identify potential neural targets, and deliver neural stimulation to potential neural target(s) to confirm that the stimulation provides a physiological response to the stimulation. Some embodiments use an accelerometer as part of mapping algorithm because the mapping electrode can be temporarily attached to the carotid sinus and the mapping algorithm can be automatically run to track the baroreflex response while evaluating extraneous stimulation using an accelerometer that serves as a sensitive sensor of motion. Additionally, the use of a multi-electrode lead provides desirable redundancy. For example, another stimulation protocol, including bipolar or unipolar stimulations, may be selected if there is a problem with the electrode configuration used to deliver therapy. Some embodiments may use a lead with one electrode (e.g. unipolar configuration) or a lead with two electrodes (e.g. bipolar configuration). The measured electrical characteristics of tissue (e.g. impedance) may be tested as the clinician moves the electrode(s) over different locations. These same electrode(s) can be used to confirm the target, and/or to deliver the therapeutic stimulation. For example, the electrodes used to test impedance may be sutured in place and then used to deliver the electrical stimulation. The anatomical mapping system may be used to map the tissue region that are tested using the electrode(s).

Figure 19:
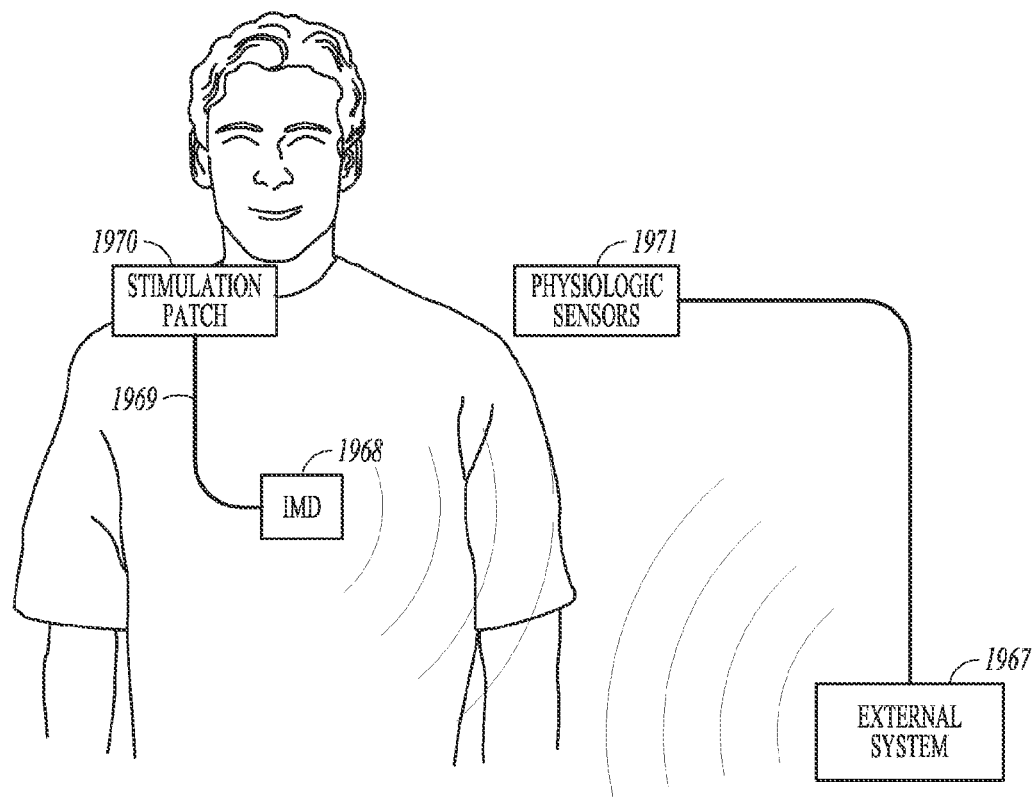
FIG. 19 illustrates, by way of example and not limitation, a system embodiment for mapping a baroreflex region which uses an external system to communicate with an implantable device to control the mapping process using the implantable device.

FIG. 19 illustrates, by way of example and not limitation, a system embodiment for mapping a baroreflex region which uses an external system 1967 to communicate with an implantable device 1968 to control the mapping process. The illustrated implantable medical device 1968 may be configured to stimulate a baroreceptor region using a lead 1969 with a stimulation patch 1970. An external system 1967 is configured to wirelessly communicate with the IMD 1968. One example of an external device is a programmer. The external system 1967 can be used to control the mapping process discussed herein. For example, the external system 1967 can instruct the IMD 1968 to measure impedance using various electrode(s), and deliver stimulation using various electrode(s). The external system 1967 can use physiologic sensors 1971 to monitor the response to the stimulation. The external system 1967 can record the mapping results, or a portion thereof, for the available electrode configurations in external memory of the external system 1967, and/or record the mapping results, or a portion thereof, for the available electrode configurations in the IMD 1968. In some embodiments, for example, the external system 1967 uses mapping results to program redundancy in the IMD 1968. The programmed redundancy identifies a different electrode configuration for use if the current stimulation configuration fails.

The present subject matter has been discussed and illustrated using specific examples where the mapped neural tissue is in the carotid sinus, and where the therapy is a stimulation of the baroreceptors in the carotid sinus. However, the mapping may be used to locate other neural tissue such as the carotid body, neural tissue in the carotid fat pads, tissue innervated by the renal nerve, the vagus nerve, the hypoglossal nerve, the carotid sinus nerve, the pulmonary artery, etc. Further, the therapy may be a therapy to stimulate nerve traffic in the neural target, or may be a therapy to reduce or block nerve traffic in the neural target. Additionally, the therapy may be a therapy to ablate neural tissue at the located neural target.

Figure 20:
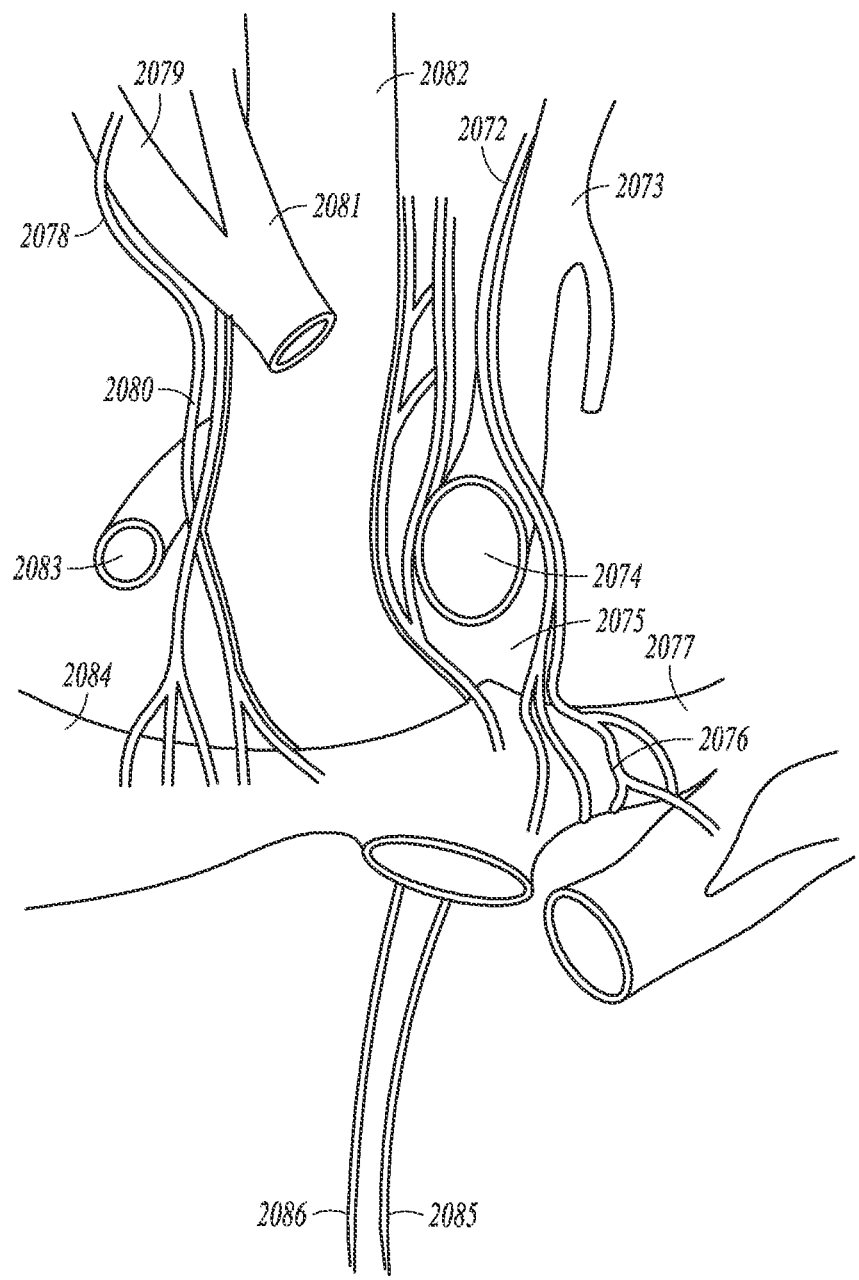
FIG. 20 generally illustrates physiology of the left and right pulmonary arteries and the left and right vagus nerves.
Figure 21:
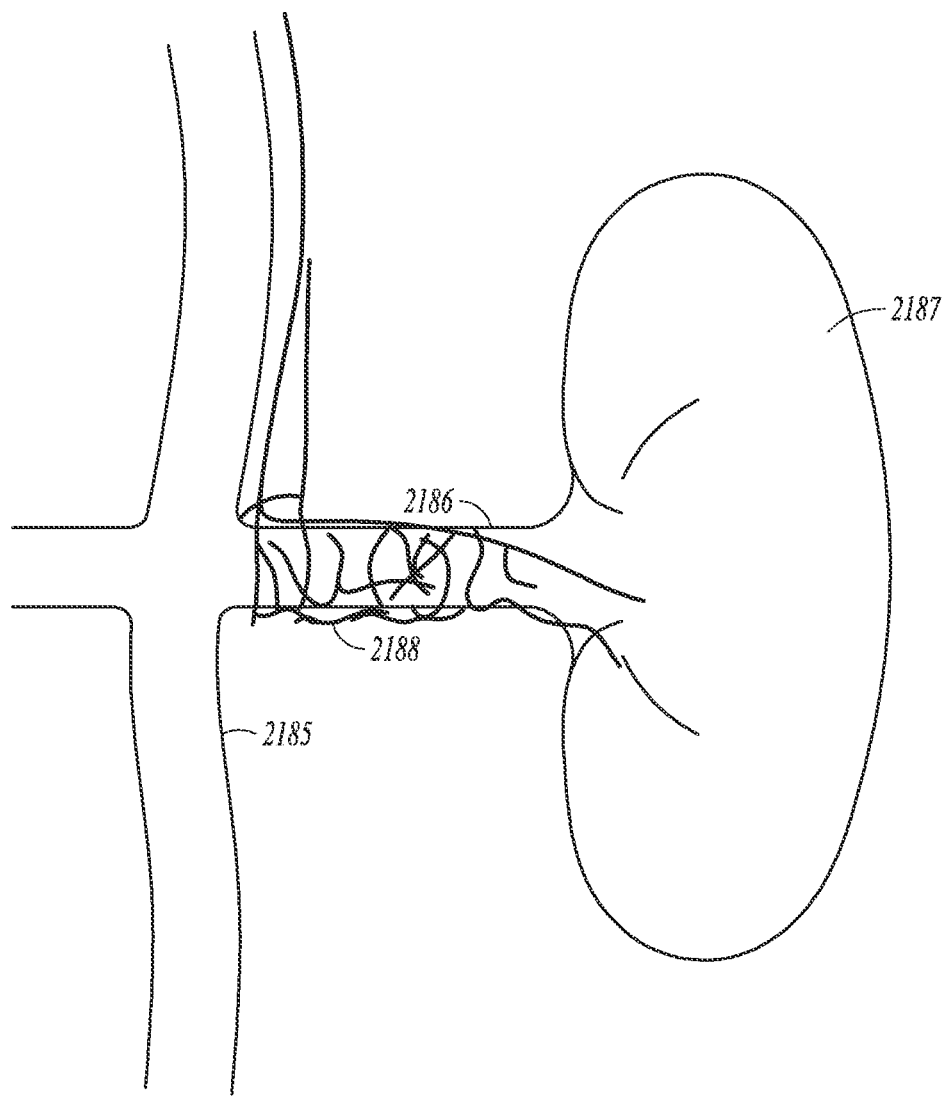
FIG. 21 generally illustrates physiology of the kidney and renal nerve.

FIGS. 20 and 21 are provided to illustrate some of the anatomical regions innervated by neural tissue in a complex manner. The present subject matter may be used to identify or locate nerves relatively quickly as it is not necessarily to observe a physiological response to stimulation to confirm that the identification of nervous tissue.

FIG. 20 generally illustrates physiology of the left and right pulmonary arteries and the left and right vagus nerves. The pulmonary artery includes baroreceptors that are innervated by the vagus nerve. Also, various branches of the vagus nerve pass the pulmonary artery. A left vagus nerve 2072 extends next to a subclavian artery 2073. Various nerves extend around the arch of the aorta 2074. Vagus nerve 101 also extends past the ligamentum arteriosum 2075. The anterior pulmonary plexus 2076 crosses the left pulmonary artery 2077. Right vagus nerve 2078 extends past a subclavian artery 2079. Cardiac nerves 2080 extend past the brachiocephalic trunk 2081 near the trachea 2082. Cardiac nerves 2080 also extend past the arch of an azygos vein 2083 to the right pulmonary artery 2084. A lower portion 2085 of the left vagus nerve 2072 and a lower portion 2086 of the right vagus nerve 2078 appear in the lower portion of FIG. 1. Thus, a number of vagal targets can be targeted within the pulmonary artery, including PA baroreceptors and some vagus nerve branches. An extravascular patch may be used to map the region to find neural tissue, or an intravascular tool may be inserted into the pulmonary artery to map the neural tissue in the region. The intravascular tool may have a stent-like shape similar to FIG. 4. The electrode region may be completely around the intravascular tool, or may be along only a portion of the intravascular tool. The neural target(s) near the pulmonary artery may be ablated or stimulated, according to various embodiments. Furthermore, some embodiments may be able to target one or more of the vagus nerve branches passing the pulmonary artery without targeting the baroreceptor region, or target the baroreceptor region without targeting the vagus nerve branches. For example, the system may be able to distinguish between the electrical tissue characteristic (e.g. impedance) of a baroreceptor region from the tissue characteristics of a vagus nerve branch passing the pulmonary artery.

FIG. 21 generally illustrates physiology of the kidney and renal nerve. Blood flows from the aorta 2185 through a renal artery 2186 to a kidney 2187. A renal nerve descends and branches out into a complex pattern of neural fibers 2188 that course along the renal artery to the kidney. Renal nerve denervation has been suggested as a method for treating hypertension. The systemic blood pressure of the patient can be reduced by ablating some of these nerves. Renal nerve ablation may involve inserting a catheter into the renal artery, and deliver radiofrequency energy to ablate some of the neural tissue. Mapping electrodes maybe incorporated near the distal end of the ablation catheter for use to map neural tissue to determine a target for ablation. The mapping electrodes may be completely around the circumference of the catheter, or may be around only a portion of the circumference. A candidate target for therapy may be stimulated (e.g. enhance or reduce or block nerve traffic at the target) and a physiological response to the stimulation may be monitored to confirm that the candidate target is appropriate for the therapy.

Another example where the present subject matter may be used to identify neural targets includes nerves that innervate the airways, such as parasympathetic ganglia at the trachies or mainstem bronchi, for example. Targeted nerves that innervate the airways may be stimulated to elicit neural activity, may be stimulated to inhibit neural activity, or may be ablated for various types of therapies.

Figure 22A:
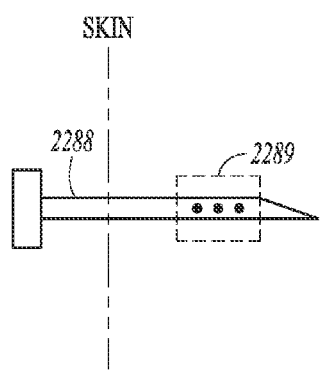
FIGS. 22A and 22B illustrate some examples of surgical tools that have a mapping electrode region.
Figure 22B:
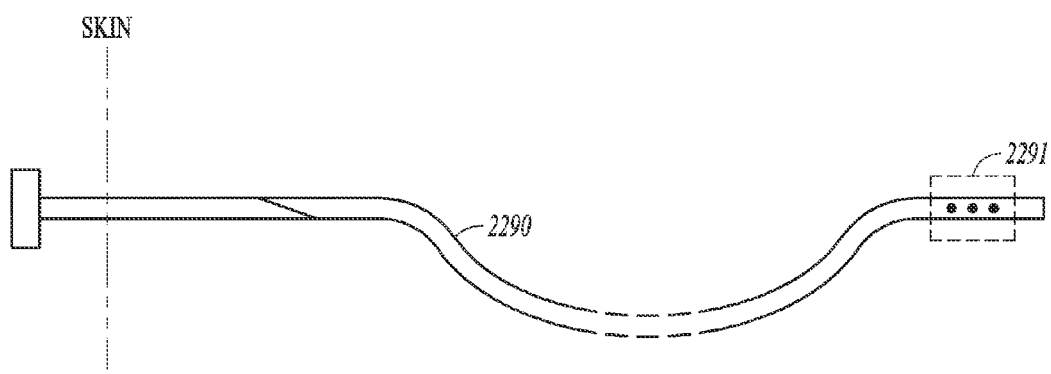

FIGS. 22A and 22B illustrate some examples of surgical tools that have a mapping electrode region. For example, FIG. 22A illustrates an introducer 2288 that has a mapping region 2289. Thus, a surgeon can insert the introducer through the patient's skin near neural tissue that is expected to contain candidate neural targets), use the mapping electrodes in the mapping region to map the tissue area to identify candidate neural target(s) within the area. A lead may be inserted though the transducer and oriented in a direction to deliver therapy toward one or more of the located neural target(s). By way of example, the therapy may include ablation, may include neural stimulation to elicit nerve traffic, or may include stimulation to inhibit nerve traffic. FIG. 22B illustrates a catheter 2290 that has a mapping electrode region 2291. The catheter 2290 can be advanced through the patient to provide the distal end near a region with neural target(s). The mapping electrode region 2291 can be used to identify neural target(s). In addition to searching along the circumference of the catheter for neural target(s), the catheter itself can be manipulated (e.g. retracted, advanced, and/or rotated) to reposition the mapping electrode region to find the neural target(s). A lead can be advanced through the catheter and oriented to deliver therapy to the neural target(s).

Such an embodiment may be useful in an intrasheath vagus nerve application. Instead of relying on other physiological responses to confirm the electrode position with respect to the VN, tissue characteristics can be measured using the mapping electrode region on the introducer or other tool to detect the neural tissue. Once the neural target(s) is (are) found, the stimulation electrodes can be oriented in the appropriate direction to stimulate the neural target(s).

Other anatomical regions innervated by neural tissue in a complex manner include epicardial ganglionated plexi (GP). GP are organized nerves present in cardiac fat pads on the epicardial surface of the heart and the ligament of Marshall, which is located between the left atrial appendage and the left pulmonary veins and is believed to be a source of AF. The GPs are part of an epicardial neural network that comprises multiple ganglia with interconnecting neurons and axons, including afferent sensory fibers and sympathetic and parasympathetic efferents.

Some therapies that may be applied to selected tissue may include neural ablation, electrical stimulation to elicit nerve traffic, or electrical stimulation to inhibit nerve traffic. For example, ablation of GP is a potential target for the treatment of AF. Endocardial RF GP ablation however leads to injury to intervening atrial myocardium, so unnecessary ablation of innocent tissue should be avoided. A discussion of GP ablation for atrial fibrillation may be found in Yong Zhang. Mei Gao, Jiangrong Wang and Yinglong Hou (2012). Ganglionated Plexi Ablation for Atrial Fibrillation, Atrial Fibrillation—Basic Research and Clinical Applications, Prof. Jong-Il Choi (Ed.), ISBN: 978-953-307-399-6, InTech, Available from: http://www.intechopen.com/books/atrial-fibrillation-basic-research-andclinical-applications/ganglionated-plexi-ablation-for-atrial-fibrillation, which is incorporated herein by reference in its entirety. This reference indicates that GPs include the anterior right GP (ARGP) at the right superior PV (RSPV)-atrial junction, the inferior right GP (IRGP) at the junction of inferior vein cava and both atria; the superior left GP (SLGP) near the left superior PV (LSPV)-atrial junction and left pulmonary artery, and inferior left GP (ILGP) at the left inferior PV (LIPV)-atrial junction. U.S. Pat. No. 7,769,446 entitled "Neural Stimulation System for Cardiac Fat Pads" and assigned to Cardiac Pacemakers, Inc. identifies some fat pad targets for therapy and is incorporated herein by reference in its entirety.

Previous methods for identifying GP locations include "blind" methods that presume anatomical locations and/or methods that deliver high frequency stimulation to the tissue and monitor for elicited dromotropic effects to the stimulation. In contrast, the present subject matter may be used to identify or locate nerves relatively quickly as it is not necessarily to observe a physiological response to stimulation to confirm that the identification of nervous tissue. Some embodiments may also deliver stimulation and observe a physiological response as an added measure to confirm the location of the neural region to be targeted. An example of such a location is a GP within a fat pad on the ligament of Marshall that is being targeted for ablation to treat AF.

Some embodiments for delivering therapy to GP may include a catheter that incorporates electrodes on the distal tip. An electrical characteristic of the tissue may be tested using the catheter. For example, some embodiments inject current into the tissue and detect the corresponding voltage to provide a measure of impedance. As the cardiac motion and fluid volume fluctuations with each heartbeat may confound measurement (e.g. tissue impedance), some embodiments may only measure the tissue characteristic (e.g. tissue impedance) during the refractory period of the local tissue. For example, some embodiments trigger impedance sensing to local tissue depolarization (P or R-waves), which minimizes both excitatory stimulation and confounding tissue volume changes. In addition, or as an alternative, to sensing during refractory periods, some embodiments may only measure impedance when the heart rate is within a desired heart rate range to reduce variability in the measurement that may be otherwise caused by motion and/or volume changes. The location of the GPs may be mapped by moving the catheter to different areas of the heart and repeating the test. A pattern of electrodes may be configured to use different sets of electrodes to map tissue. In addition, the pattern may use one or more levels of electrode subsets to map the tissue. The tests performed at the different locations can be used to identify the GP locations, and these locations can be labeled on an anatomical map. Some embodiments may confirm potential GP locations by delivering electrical stimulation to the tissue and monitoring for a physiological response to the electrical stimulation. Some embodiments may use the same catheter used to identify the GP location to also ablate a desired GP location that had been identified by the tests. Some embodiments may use another catheter than the one used to identify the GP locations to ablate a desired GP location identified by the tests.

The present subject matter allows strategic therapeutic targeting of arrhythmogenic areas of the heart, while limiting unnecessary ablation of tissue. Some embodiments may use the anatomical map and another catheter to deliver the ablation energy. Some embodiments may deliver neural stimulation to elicit nerve traffic at a targeted GP location. Some embodiments may deliver neural stimulation that inhibits nerve traffic at the targeted GP location.

Figure 23A:
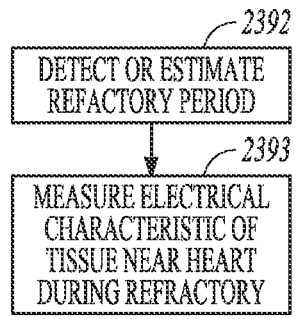
FIGS. 23A-C are examples of methods that may be performed to measure tissue characteristics on or near a heart such as may be performed to locate epicardial ganglionated plexi.
Figure 23B:
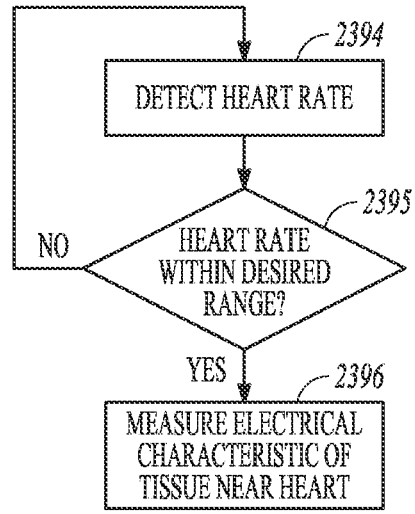
Figure 23C:
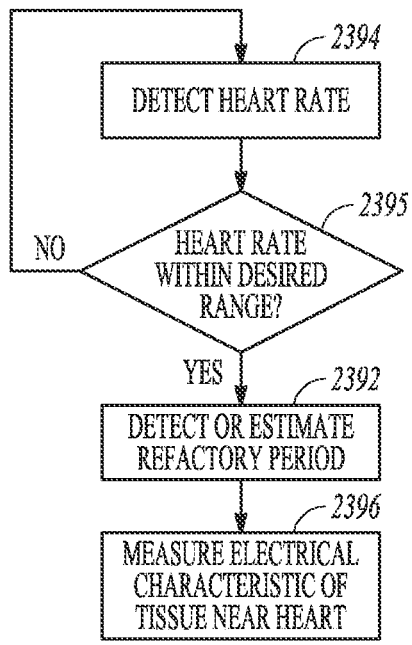

FIGS. 23A-C are examples of methods that may be performed to measure tissue characteristics on or near a heart such as may be performed to locate epicardial ganglionated plexi. In the example illustrated in FIG. 23A, a refractory period of the heart is determined at 2392. The refractory period may be positively detected by cardiac sensors. The system may be configured to estimate refractory periods from previously-sensed cardiac activity. For example, the system may be able to periodically estimate refractory periods for a given cardiac cycle and some subsequent cardiac cycles based on a sensed R wave and a detected heart rate. At 2393, the electrical characteristic of the heart is measured during the refractory. This process may be repeated to map a tissue region using electrical characteristics that were measured during refractory periods. In the example illustrated in FIG. 23B, the system may detect a heart rate at 2394. For example, the heart rate may be detected using electrodes to detect electrical signals from the heart, acoustic sensors to sense heart sounds, or blood pulse parameters (e.g. blood flow and/or pressure). If the heart rate is within a desired range at 2395, the system may proceed to measure the electrical characteristic of the tissue on or near the heart at 2396. In the example illustrated in FIG. 23C, the system may detect a heart rate at 2394. If the heart rate is within a desired range at 2395, the system may proceed determine (e.g. detect and/or estimate) refractory period(s) at 2392, and to measure the electrical characteristic of the tissue on or near the heart at 2396 during the refractory and while the heart rate is within the desired range. These examples of methods that may be performed to measure tissue characteristics on or near a heart promote consistent measurements of tissue that are less affected by the motion and/or volume changes of the heart.

Figure 24:
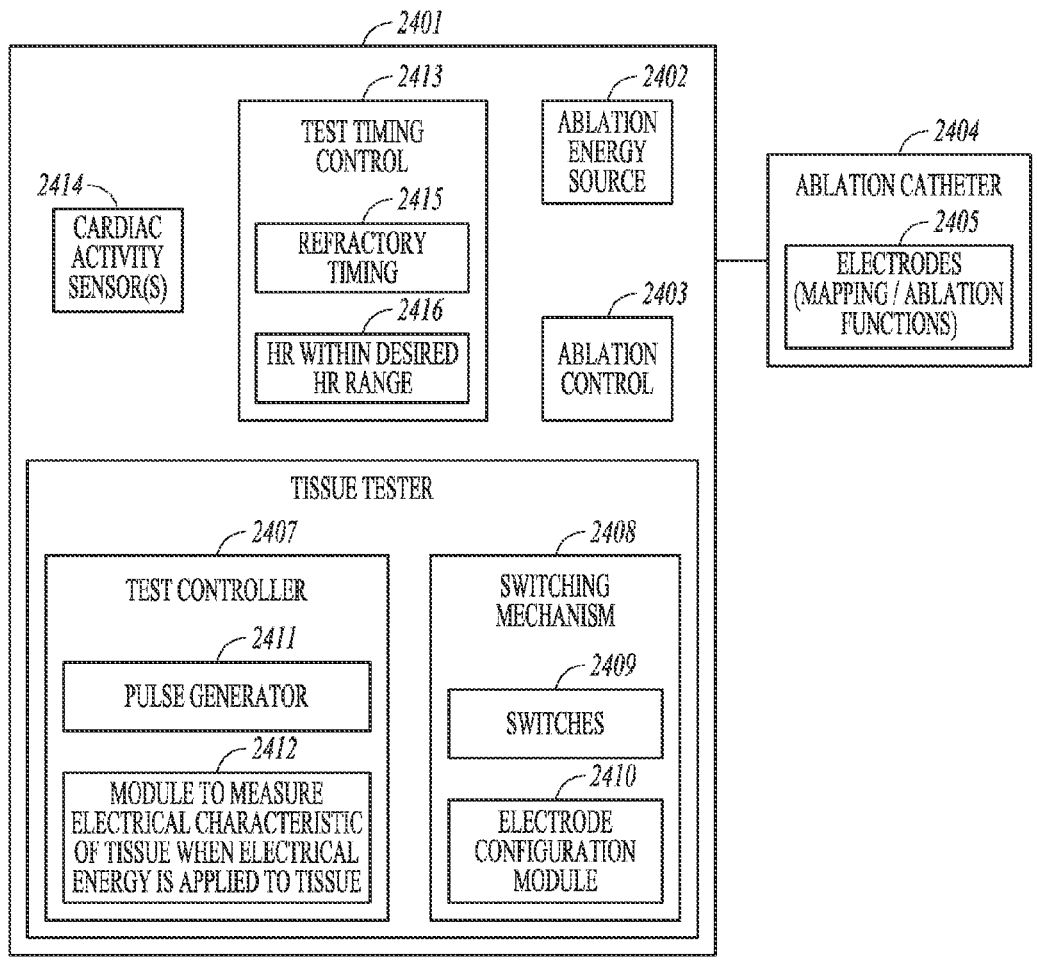
FIG. 24 illustrates a system configured to test tissue on or near the heart, and further configured to deliver a therapy such as an ablation therapy to the heart.

FIG. 24 illustrates a system configured to test tissue on or near the heart, and further configured to deliver a therapy such as an ablation therapy to the heart. The illustrated system includes an ablation system 2401 with an ablation energy source (e.g. radiofrequency (RF) energy for RF ablation) and an ablation control. Those of ordinary skill in the art will appreciate, upon reading and understanding this disclosure, that the illustrated system may be modified to deliver electrical stimulation to elicit nerve traffic, or electrical stimulation to inhibit nerve traffic as an alternative to the ablation therapy or in addition to the ablation therapy. The ablation system 2401 is capable of being connected to an ablation catheter 2404. The catheter 2404 includes electrodes which may be configured to map the tissue region and/or to ablate a portion of the tissue region. The system includes a tissue tester 2406, similar to that illustrated in FIG. 5. The tissue tester 2406 includes a test controller 2407 and a switching mechanism 2408 configured to connect electrode(s) to the test controller 2407. The test controller 2407 may include a pulse generator 2411 configured to deliver electrical neural stimulation using two conductors. The switching mechanism 2408 includes switches 2409 and an electrode configuration control 2410 that may be configured to control the switches to select the electrode(s) to function as the anode and the electrode(s) to function as the cathode for bipolar stimulation. The illustrated test controller 2407 may also include a module 2412 configured to measure an electrical characteristic (or characteristics) of tissue when electrical energy is applied to the tissue. By way of example and not limitation, the measured electrical characteristic may be resistance, impedance or permittivity. The illustrated system 2401 further includes test timing control module 2413 which is configured to control when to test the tissue to avoid the cardiac activity from adversely affecting the test. For example, the test timing control module 2413 may receive cardiac activity information from a cardiac activity sensor(s) 2414. The test timing control module 2413 may use the sensed cardiac activity to determine refractory timing 2415 and/or to determine if heart rate is within a desirable range. The test timing control module 2413 may be configured to allow the tissue test to be performed only during a refractory period, or only when the heart rate is within a desired range, or only when the heart rate is within a desired range and when the heart is in a refractory period. It is understood that the illustrated portions of the system are provided as an example, that the system may be implemented using various combinations of hardware, software and firmware.

The above detailed description is intended to be illustrative, and not restrictive. Other embodiments will be apparent to those of ordinary skills in the art upon reading and understanding the above description. By way of example and not limitation, target muscle fibers may be found by mapping measurements of the electrical characteristics of tissue (e.g. tissue impedance). These muscle fibers may be smooth, skeletal, or cardiac. An appropriate therapy may be delivered to a region determined using these mapping measurements. The scope of the disclosure should, therefore, be determined with references to the appended claims, along with the full scope of equivalents to which such claims are entitled.

What is claimed is:

1. A method for identifying a neural target, comprising:
    implanting a patch of electrodes, including placing a set of electrodes on tissue containing neural tissue, the set of electrodes including subsets of two or more electrodes;
    measuring an electrical characteristic of tissue using the subsets within the set of electrodes placed on the tissue, the electrical characteristic of tissue quantifying an ability of the tissue to oppose or to conduct an electric current or an ability of the tissue to transmit an electric field; and
    comparing measurements and identifying a subset of electrodes that that provides a more desirable measurement of the electrical characteristic than other subsets of electrodes to identify the neural target, wherein the more desirable measurement is a measurement that has a lower ability to oppose the electric current, or a higher ability to conduct the electric current, or a higher ability to transmit an electric field.

2. The method of claim 1, wherein identifying the subset of electrodes that has a more desirable measurement of the electrical characteristic includes identifying the subset of electrodes that has the lowest tissue impedance or tissue resistance to identify the neural target.

3. The method of claim 1, wherein placing the set of electrodes on tissue containing neural tissue includes placing the set of electrodes on tissue in a carotid sinus region.

4. The method of claim 1, wherein placing the set of electrodes on tissue containing neural tissue includes placing the set of electrodes on a baroreceptor region.

5. The method of claim 1, wherein placing the set of electrodes on tissue containing neural tissue includes placing the set of electrodes on tissue containing a peripheral nerve trunk.

6. The method of claim 1, wherein placing the set of electrodes on tissue containing neural tissue includes placing the set of electrodes on tissue containing autonomic neural tissue.

7. The method of claim 1, wherein placing the set of electrodes on tissue containing neural tissue includes placing the set of electrodes on a cardiac fat pad.

8. The method of claim 1, wherein placing the set of electrodes on tissue containing neural tissue includes placing the set of electrodes on tissue in a pulmonary artery region.

9. The method of claim 1; wherein placing the set of electrodes on tissue containing neural tissue includes placing the set of electrodes on tissue containing motor neural tissue.

10. The method of claim 1, further comprising confirming the neural target, wherein confirming the neural target includes:
    stimulating the neural target; and
    monitoring a physiological response confirming stimulation of the neural target.

11. The method of claim 10, further comprising monitoring for undesired capture of adjacent tissue.

12. The method of claim 1, further comprising recording the measurements for each of the subsets.

* * * * *